US011390586B2

(12) United States Patent
Andrén et al.

(10) Patent No.: US 11,390,586 B2
(45) Date of Patent: Jul. 19, 2022

(54) PYRIDINIUM, QUINOLINIUM, ACRIDINIUM, PYRYLIUM, CHROMENYLIUM OR XANTHYLIZUM REACTIVE DESORPTION AND/OR LASER ABLATION IONIZATION MATRICES AND USE THEREOF

(71) Applicants: Per Andrén, Uppsala (SE); Luke Odell, Uppsala (SE); Anna Nilsson, Uppsala (SE); Mohammadreza Shariatgorji, Stockholm (SE); Jonas Sävmarker, Uppsala (SE)

(72) Inventors: Per Andrén, Uppsala (SE); Luke Odell, Uppsala (SE); Anna Nilsson, Uppsala (SE); Mohammadreza Shariatgorji, Stockholm (SE); Jonas Sävmarker, Uppsala (SE)

( * ) Notice: Subject to any disclaimer, the term of this patent is extended or adjusted under 35 U.S.C. 154(b) by 0 days.

(21) Appl. No.: 16/978,619

(22) PCT Filed: Mar. 6, 2019

(86) PCT No.: PCT/SE2019/050197
§ 371 (c)(1),
(2) Date: Sep. 4, 2020

(87) PCT Pub. No.: WO2019/172830
PCT Pub. Date: Sep. 12, 2019

(65) Prior Publication Data
US 2020/0407317 A1 Dec. 31, 2020

(30) Foreign Application Priority Data
Mar. 7, 2018 (SE) .................. 1850249-2

(51) Int. Cl.
| C07D 213/04 | (2006.01) |
| C07D 213/61 | (2006.01) |
| C07D 213/68 | (2006.01) |
| C07D 213/73 | (2006.01) |
| C07D 215/18 | (2006.01) |
| C07D 409/04 | (2006.01) |
| H01J 49/04 | (2006.01) |

(52) U.S. Cl.
CPC ......... *C07D 213/04* (2013.01); *C07D 213/61* (2013.01); *C07D 213/68* (2013.01); *C07D 213/73* (2013.01); *C07D 215/18* (2013.01); *C07D 409/04* (2013.01); *H01J 49/0418* (2013.01)

(58) Field of Classification Search
CPC .. C07D 213/04; C07D 213/61; C07D 213/68; C07D 213/73; C07D 215/18; C07D 409/04; H01J 49/0418
See application file for complete search history.

(56) References Cited

U.S. PATENT DOCUMENTS

| 7,338,428 B2 * | 3/2008 | Chang ................... C09B 23/145 506/15 |
| 7,790,896 B2 | 9/2010 | Chang et al. |
| 2004/0152739 A1 * | 8/2004 | Anderson et al. ........ A61P 1/04 514/341 |

FOREIGN PATENT DOCUMENTS

| EP | 00006359 A1 | 1/1980 |
| WO | 03/031983 A2 | 4/2003 |

OTHER PUBLICATIONS

Anderson et al., 61(51) Tetrahedron 12033-12041 (2005) (CAS Abstract) (Year: 2005).*
Weber H: "Die Decker-Oxidation 2-substituierter N-Alkylpyridiniumverbindungen, 3. Mitt.: Zur Kenntnis der isomeren 1-Methyl-2-phenyl-pyridone", Archiv Der Pharmazie vol. 398, No. 8 vol. 398, No. 8 Jan. 1, 1975 (Jan. 1, 1975), pp. 637-643, XP009512713, Wiley Verlag, Weinheim ISSN: 9365-6233, DOI :10.1002/ARDP.19753080810.
Leanne Beer et al: "The effect of selenium incorporation on the bandwidth and conductivity of neutral radical conductors",Chemical Communications, No. 46, Jan. 1, 2005 (Jan. 1, 2005), p. 5745, XP055582215, ISSN: 1359-7345, DOI: 10.1039/b511648a compound 3.
(Continued)

*Primary Examiner* — Timothy R Rozof
(74) *Attorney, Agent, or Firm* — Casimir Jones S. C.; Lisa Mueller

(57) ABSTRACT

The present disclosure concerns use of compounds of formula I, or salts thereof, as reactive matrices for desorption and laser ablation ionization spectrometry. The disclosure further concerns compounds of formula II, or salts thereof, and use of compounds of formula II or III, or salts thereof.

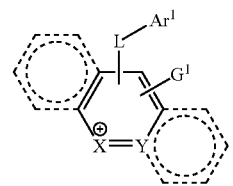

(I)

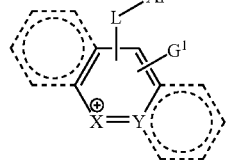

(II)

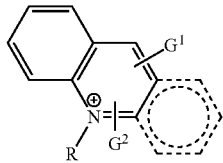

(III)

7 Claims, 6 Drawing Sheets

(56) References Cited

OTHER PUBLICATIONS

Ruiz, Anthony et al: "Pyridinium Chloride: a New Reagent forN-Demethylation of N-Methylazinium Derivatives", Tetrahedron Letters, vol. 38, No. 35, Jan. 1, 1989 (Jan. 1, 1989), pp. 6205-6208, XP085609582, ISSN: 0040-4039, DOI :10.1016/S0040-4039 (97) 01399-3 compound 1.

Meth-Cohn et al: "The reverse vilsmeier approach to the synthesis of quinolines, quinolinium salts and quinolones", Tetrahe, Elsevier Science Publishers, Amsterdam , NL, vol. 51, No. 47, Nov. 20, 1995 (Nov. 20, 1995), pp. 12869-12882, XP005254730, ISSN: 0040-4020, DOI : 10.1016/0040-4020(95) 00729-R Table on p. 12879, products of formula 3—2nd, 3rd, 4th and 19th compounds.

Elzet Stander-Grobler et al: "Amine-substituted-N(standard)- and -N(remote)-pyridylidene complexes Synthesis and bonding",Inorganica Chimica Acta, Elsevier BV, NL, vol. 376, No. 1, May 31, 2911 (May 31, 2011), pp. 87-94, XP028292881, ISSN: 0020-1693, DOI :10.1016/J . ICA.2011.05.038 compound 5ii.

Andrzej Zieba et al: 1-ALkyl-4-(arylamino) quinolinium-3-thiolates and 7-Alkyl-12H-quino [3,4-b]-1,4 benzothiazini um Salts European Journal of Organic Chemistry, vol. 2000, No. 16,Aug. 1, 2000 (Aug. 1, 2000), pp. 2947-2953, XP055583664,DE ISSN: 1434-193X,DOI :10.1002/1099-0690 ( 200008) 2000:16<2947: : AID-EJOC2947>3.0.C0;2-U; compounds 5a, 5b, 12 compounds 5a, 5b, 12.

Hubertus Ahlbrecht et al: Synthese Von Chinolinderivaten Durch Acylierung Von N-Aryl-Carbonsaeureamiden Und N-Aryl-Enaminen Mit Phosgen II, Chem . BER, vol. 108, Jan. 1, 1975 (Jan. 1, 1975), pp. 2300-2311, XP055552893, DOI: 10.1002/cber. 19751080718 compound 2b.

Wayne K Anderson et al: "Synthesis,Chemistry, and Antineoplastic Activity of Alpha-Halopyridinium Salts: Potential Pyridone Prodrugs of Acylated Vinylogous Carbinolamine Tumor Inhibitors1", J . Med. Chem, vol. 33, Jan. 1, 1990 (Jan. 1, 1990), pp. 1667-1675, XP055583701, compounds 14-18.

Michael S. Bereman et al: "Increasing the hydrophobicity and electrospray response of glycans through derivatization with novel cationic hydrazides", Chemical Communications, vol. 46, No. 2 , Jan. 1, 2019 (Jan. 1, 2019), pp. 237-239, XP055582872, ISSN: 1359-7345, DOI: 10.1039/B915589A Reagent 2; p. 237, col. 1, paragraph 3rd; figures 1,2,3 Paragraph bridging cols. 1 and 2; p. 237.

Shariatgorji, Mohammadreza et al: "Pyrylium Salts as Reactive Matrices for MALDI-MS Imaging of Biologically Active Primary Amines", Journal of the American Society for Mass Spectrometry, vol. 26, No. 6, Mar. 28, 2015 (Mar. 28, 2015), pp. 934-939, XP035498792, Elsevi Er Science Inc, US ISSN: 1944-9395, DOI: 10.1007/013361-015-1119-9 [retrieved on Mar. 28, 2015] cited in the application p. 937, paragraph Results and Discussion—p. 938; figure 1; compounds PDBDPP, DPP the whole document.

Barry S J et al: "Derivatisation for Liquid Chromatography/ Electrospray Mass Spectrometry: Synthesis of Pyridinium Compounds and Their Amine Carboxylic Acid Derivatives", Rapid Communications in Mass Spectrometry, Jan. 1, 2003 (Jan. 1, 2003), pp. 503-620, XP009058417,John Wiley & Sons, CIB ISSN: 0951-4198, DOI: 10.1002/ RCM.957 figures 1, 3, 5, 6, 19, 14; compounds 2 , the whole document.

Gerasloma M R et al: "The Viologen Cation Radical Pimer: A case of dispersion-driven bonding", Angewandte Chemie, International Edition, , vol. 56, No. 32, Jan. 1, 2017 (Jan. 1, 2017), pp. 9435-9439, XP009514750, Wiley-VCH, DE; ISSN: 1433-7851, DOI: 10.1002/ ANIE.201704959 compound 13.

Clennan, Edward L. et al: Synthesis, Characterization, Photophysics and Photochemistry of Pyrylogen Electron Transfer Sensitizers, Photochemistry and Photobiology, , vol. 90, No. 2, Mar. 1, 2014 (Mar. 1, 2014), pp. 344-357,XP009514697, ISSN: 0031-8655, DOI: 10.1111/PHP .12174 Scheme 1—compound wuth X=C1 ; p. 345.

Kniep F et al: "4,4' —azobis (halopyridinium) derivatives: Stron multidentate halogen-bond donors with a redox-active core", Chemistry—A European Journal, vol. 18, No. 5 ;Jan. 1, 2012 (Jan. 1, 2012), pp. 1306-1310, XP009514753, Wiley-V C H Verlag GMBH & Co. KGAA, DE ISSN: 0947-6539, DOI: 10. 1002/CHEM. 201103071.

Zhang D et al: "Syntheses, characterizations, and properties of electronically perturbed 1, 1'-dimethyl-2,2'-bipyridinium tetrafluoroborates", Journal of Organic Chemistry, vol. 71, No. 1;Jan. 1, 2006 (Jan. 1, 2006), pp. 315-319, XP009514754,American Chemical Society, US ISSN: 0022-3263, DOI : 10. 1021/ J00521271.

Fuku-En S. et al: "Oxidation of an allene compound bearing 1,8-dichloroacridiene moieities and photolysis of the halogenated allene compound for the generation of triplet carbenes", Journal of Physical Organic Chemistry, vol. 28, No. 2 ,Jan. 1, 2015 (Jan. 1, 2015), pp. 79-87, XP009514751, John Wiley & Sons Ltd, GB ISSN: 1099-1395 compounds 5c, 5d, 6c.

Galanakis et al: "Synthesis and quantitative structure-activity relationship of a novel series of small conductance Ca2+-activated K+ channel blockers related to dequalinium", Journal of Medicinal Chemistry, vol. 39, No. 2,Jan. 1, 1996 (Jan. 1, 1996), pp. 359-370, XP009514755, compounds 21, 2a.

Rosania, Gustavo R et al: "Combinatorial Approach to Organelle-Targeted Fluorescent Library Based on the Styryl Scaffold", Journal of the American Chemical Society, American Chemical Society, vol. 125, No. 5, Feb. 5, 2003 (Feb. 5, 2003), pp. 1130-1131, XP009514702, ISSN: 0002-7863, DOI: 10 . 1021/JA027587X compounds F23, F24, F28, F32-34, F38, F41.

Novikov, V. N. et al: "Synthesis and spectral properties of furyl-substituted pyridines and pyrylium and pyridinium salts" Chemistry of Heterocyclic Compounds, vol. 24, No. 10, Jan. 1, 1988 (Jan. 1, 1988), pp. 1091-1094, XP009514748, DOI: 10. 1007/BF00475680 compounds Ia, Ib, Ic, IVa.

Vogel A I ; Furni ss B S; Hannaford A J ; Smith P W G; Tatchell A R: "Spectroscopic Methods and the Interpretation of Spectra",Jan. 1, 1989 (Jan. 1, 1989), Vogel's Textbook of Practical Organic Chemistry,Addison Wesley Longman Limited, Harlow, XP002790838,ISBN: 978-0-582-46236-6 pp. 383-384, Isotope patterns; p. 384; figure 5.80.

* cited by examiner

PYRIDINIUM, QUINOLINIUM, ACRIDINIUM, PYRYLIUM, CHROMENYLIUM OR XANTHYLIZUM REACTIVE DESORPTION AND/OR LASER ABLATION IONIZATION MATRICES AND USE THEREOF

CROSS-REFERENCE TO RELATED APPLICATIONS

This application is a 35 U.S.C. § 371 national stage application for International Application No. PCT/SE2019/050197, filed on Mar. 6, 2019, entitled "PYRIDINIUM, QUINOLINIUM, ACRIDINIUM, PYRYLIUM, CHROMENYLIUM OR XANTHYLIZUM REACTIVE DESORPTION AND/OR LASER ABLATION IONIZATION MATRICES AND USE THEREOF", the disclosures and contents of which are hereby incorporated by reference in their entireties.

TECHNICAL FIELD

The present invention relates to organic chemical compounds and the use of such compounds as reactive matrices for desorption and/or laser ablation ionization spectrometry.

BACKGROUND ART

Advanced mass spectrometry techniques have revolutionised the analysis of biomolecules. Koichi Tanaka was awarded the Nobel Prize in Chemistry 2002 for his development of soft laser desorption techniques in mass spectrometry. These developments laid the foundation for many of today's powerful mass spectrometry (MS) techniques that utilize laser desorption and/or ablation ionization, including one of the most widely utilized technique for the MS analysis of macromolecules: Matrix-Assisted Laser Desorption Ionization (MALDI-MS).

MALDI principally relies on co-crystallization of an excess amount of an assisting matrix with an analyte. A shallow layer of the resulting crystal is ablated by irradiation from a short laser pulse, which consequently results in partial ionization and detection of the sample. It has been well established that an efficient assisting matrix must exhibit strong optical absorption at the wavelength of the pulsed laser (typically 337 nm for nitrogen or 355 nm for Nd:YAG laser). Moreover, it needs to efficiently co-crystallize with the analyte molecule(s) after the evaporation of the solvent, and facilitate cationization (protonation) of the analyte in the gas phase. For that reason most commonly used positive ion mode MALDI-MS matrices e.g. alpha-cyano-4-hydroxycinnamic acid (CHCA) and 2,5-dihydroxybenzoic acid (DHB) are acidic compounds to facilitate proton transfer and they have a high optical absorptivity in the range of 290-370 nm to transfer the laser energy to the analyte.

MALDI and similar techniques use a laser energy absorbing matrix in order to volatilize and ionize sample molecules for subsequent detection by a mass spectrometer. An analyte is mixed with an excess amount of a suitable matrix material, which is commonly a cinnamic acid, benzoic acid or picolinic acid derivative. A laser is then used to irradiate the matrix/analyte mixture. The matrix typically has a strong optical absorption at the wavelength of the laser, thus assisting in desorption and ablation at the surface of the matrix/analyte crystal. The analyte molecules now in the gas phase are then typically protonated by the acidic gas phase matrix molecules, and the resulting charged analyte molecules can then be accelerated to a mass spectrometer operating in positive ion mode. Many classes of compounds may be analysed by MALDI-MS including but not limited to proteins, peptides, nucleotides, oligonucleotides, lipids, polysaccharides and oligosaccharides, not to mention small molecules such as metabolites and neurotransmitters.

MALDI and similar techniques may even be used as an imaging technique (mass spectrometry imaging, MSI) for identifying and mapping the distribution of molecules in tissue sections with near-cellular spatial resolution.

However MALDI-MS and MSI suffer from a number of drawbacks, including relative insensitivity towards certain compound classes and signal interference by the MALDI matrix in the low molecular weight region (100-600 Da). In order to address these problems the use of pyrylium salts such as 2,4-diphenyl-pyranylium tetrafluoroborate (DPP-TFB) has been investigated for in-situ chemical derivatization of primary amines, such as neurotransmitters. This work is described in Shariatgorji et al. Neuron 2014, 84, 697-707, and Shariatgorji et al. J. Am. Soc. Mass Spectrom. 2015, 26(6), 934-939. DPP-TFB reacts selectively with primary amines to produce N-alkyl or N-aryl pyridinium derivatives under mild conditions. These charged derivatives have adequate laser desorption and ionization efficiencies, thus enabling the detection of endogenous small-molecule primary amines such as various neurotransmitters. Moreover, the DPP-TFB derivatives undergo self-assisted laser desorption ionization, i.e. no separate matrix molecules are required as the DPP-TFB salt itself acts as a "reactive matrix".

There still remains a need for improved methods of ionizing molecules for detection with mass spectrometry.

SUMMARY OF THE INVENTION

The inventors of the present invention have identified a number of shortcomings with prior art methods of ionizing molecules by desorption and/or laser ablation for mass spectrometry.

In the prior art a diphenyl derivative of pyrylium (DPP) has been used as a reactive matrix for MALDI and MALDI-MSI of primary amine containing groups. However, a broad range of small molecules such as pharmaceuticals and their metabolites, endogenous metabolites, neurotransmitters and their metabolites, biomarkers, toxins and natural compounds do not contain primary amines and thus are not amenable to this technique. Moreover, the use of DPP requires intensive incubation in a chamber saturated by 50% methanol. This increases the risk of spreading of the sample in MALDI-MS and delocalization of target compounds in MALDI-MSI. The latter problem is very limiting for the spatial resolution obtainable in MALDI-MSI. Furthermore, pyrylium-based reactive matrices such as DPP lack effective means of identifying the ions generated.

It is an object of the present invention to provide means for desorption and/or laser ablation that overcome or at least alleviate one or more of the above mentioned drawbacks.

These objects are achieved by use of a compound of formula I according to the appended claims as a reactive matrix for desorption and/or laser ablation ionization spectrometry.

The compound of formula I has the following structure:

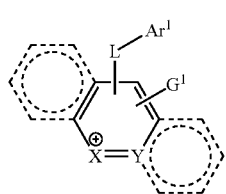
(I)

wherein

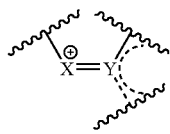

is selected from the group consisting of

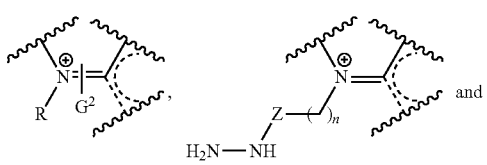

—Ar¹ is optionally substituted and is selected from the group consisting of phenyl, biphenyl, terphenyl, $C_{10}$-$C_{30}$ polycyclic aromatic hydrocarbon and $C_4$-$C_{30}$ mono- or polycyclic heteroaryl;

-L- is selected from a bond, —$(CH_2)_m$— or any π-conjugating linker moiety;

-G¹ is selected from —H, -Me or —Ar²;

—R is a $C_1$-$C_{15}$ alkyl group optionally labelled with one or more D, T, or $^{13}C$ atoms;

-G² is selected from the group consisting of —F, —Cl, —Br, —I, —$NO_2$, —CN, —OR', —OC(O)R', —SR', —S(O)R', —S(O)(O)R', —NR'R" and —$(CH_2)_n$—Z—NH—$NH_2$;

—R' and —R" are each independently selected from phenyl, tolyl and $C_1$-$C_{15}$ alkyl;

m and n are each independently from 0 to 15;

—Z— is selected from a bond, —$CH_2$— or —C(O)—;

-G³ is selected from —H, -Me or —Ar³;

each of —Ar² and —Ar³ is optionally independently substituted and is independently selected from the group consisting of phenyl, biphenyl, terphenyl, $C_{10}$-$C_{30}$ polycyclic aromatic hydrocarbon, and $C_4$-$C_{30}$ mono- or polycyclic heteroaryl;

with the proviso that when

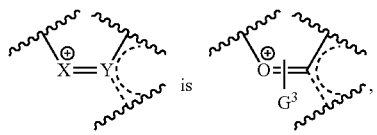

then at least one of Ar¹, Ar² or Ar³ is substituted by chlorine, bromine, deuterium or tritium.

Use of a compound of formula I as defined above as a reactive matrix for desorption and/or laser ablation ionization mass spectrometry has a number of advantageous features. The reactive matrices may target a number of substances not previously accessible with previously known reactive matrices. So, for example, as well as primary amines, the reactive matrices may react with secondary amines, phenolic hydroxides, aldehydes and ketones. The reactive matrices may not require any incubation, with the reaction occurring upon adding/spotting/spraying the reactive matrix onto the sample, without any need for cooling or heating. All of the reactive matrices form a charged derivative upon reaction with a target molecule, thus increasing the mass spectrometric sensitivity to the target molecule. Moreover, other identification means, such as specific isotope labels, may be introduced into the reactive matrix.

The compound of formula I may have a formula Ia or Ib,

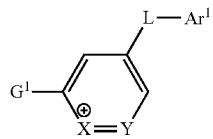
(Ia)

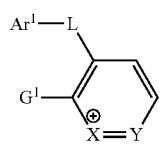
(Ib)

wherein

is selected from the group consisting of

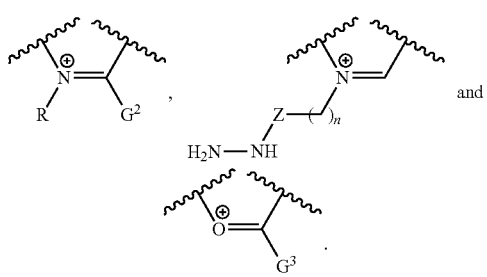

According to another aspect, the objects of the invention are achieved by a compound of formula according to the appended claims.

The compound of formula II has the following structure:

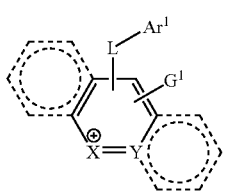
(II)

wherein

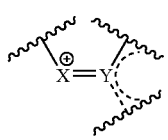

is selected from the group consisting of

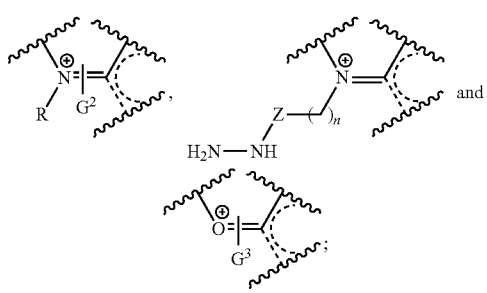

—Ar¹ is optionally substituted and is selected from the group consisting of biphenyl, terphenyl, $C_{10}$-$C_{30}$ polycyclic aromatic hydrocarbon and $C_6$-$C_{30}$ poly-cyclic heteroaryl;
-L- is selected from a bond, —(CH$_2$)$_m$— or any π-conjugating linker moiety;
-G¹ is selected from —H, -Me or —Ar²;
—R is a $C_1$-$C_{15}$ alkyl group optionally labelled with one or more D, T, or $^{13}$C atoms;
-G² is selected from the group consisting of —F, —Cl, —Br, —I, —NO$_2$, —CN, —OR', —OC(O)R', —SR', —S(O)R', —S(O)(O)R', —NR'R" and —(CH$_2$)$_n$—Z—NH—NH$_2$;
—R' and —R" are each independently selected from phenyl, tolyl and $C_1$-$C_{15}$ alkyl;
m and n are each independently from 0 to 15;
—Z— is selected from a bond, —CH$_2$— or —C(O)—;
-G³ is selected from —H, -Me or —Ar³;
each of —Ar² and —Ar³ is optionally independently substituted and is independently selected from the group consisting of phenyl, biphenyl, terphenyl, $C_{10}$-$C_{30}$ polycyclic aromatic hydrocarbon, and $C_4$-$C_{30}$ mono- or polycyclic heteroaryl;
with the proviso that when

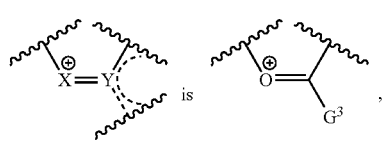

then
-L-Ar¹ is located at the 4-position of the pyrylium ring; and
at least one of Ar¹, Ar² or Ar³ is substituted by chlorine, bromine, deuterium or tritium.

By located at the 4-position of the pyrylium ring, it is meant located at the ring position diametrically opposite the oxygen of the pyrylium ring, regardless of whether the pyrylium ring is a monocyclic pyrylium, benzopyrylium or dibenzopyrylium ring system. The advantages of the compounds of formula II are analogous to the advantages of using a compound of formula I as a reactive matrix for desorption and/or laser ablation ionization spectrometry as described above. Moreover, the compounds of formula I and/or may find use in further spectroscopic or spectrometric methods where tagging a molecule with a chromophore and/or charge-tagging a molecule may prove useful. Such methods include UV spectroscopy and UV imaging, as well as other mass spectroscopic methods such as electrospray ionization.

The compound of formula II may have a formula IIa or IIb,

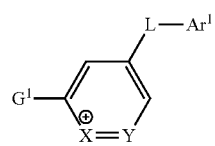
(IIa)

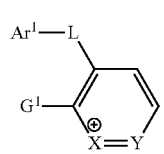
(IIb)

wherein

is selected from the group consisting of

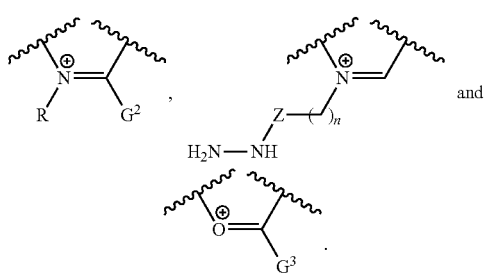

According to a further aspect, the objects of the invention are achieved by use of a compound of formula III according to the appended claims, as a reactive matrix for desorption and/or laser ablation ionization spectrometry.

The compound of formula III has the following structure:

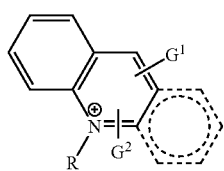

(III)

wherein:
-G$^1$ is selected from —H, -Me or —Ar$^2$;
—R is a C$_1$-C$_{15}$ alkyl group optionally labelled with one or more D, T, or $^{13}$C atoms;
-G$^2$ is selected from the group consisting of —F, —Cl, —Br, —I, —NO$_2$, —CN, —OR', —OC(O)R', —SR', —S(O)R', —S(O)(O)R', and —NR'R" and —(CH$_2$)$_n$—Z—NH—NH$_2$;
—R' and —R" are each independently selected from phenyl, tolyl and C$_1$-C$_{15}$ alkyl;
m and n are each independently from 0 to 15;
—Z— is selected from a bond, —CH$_2$— or —C(O)—;
-G$^3$ is selected from —H, -Me or —Ar$^3$; and
each of —Ar$^2$ and —Ar$^3$ is optionally independently substituted and is independently selected from the group consisting of phenyl, biphenyl, terphenyl, C$_{10}$-C$_{30}$ polycyclic aromatic hydrocarbon, and C$_4$-C$_{30}$ mono- or polycyclic heteroaryl.

The advantages of the compounds of formula III are analogous to the advantages of using a compound of formulas I or II as a reactive matrix for desorption and/or laser ablation ionization spectrometry as described above. However, compounds of formula III may have the further advantages of improved atom economy and/or ease of manufacture.

The compound of formula III may have a formula IIIa or IIIb.

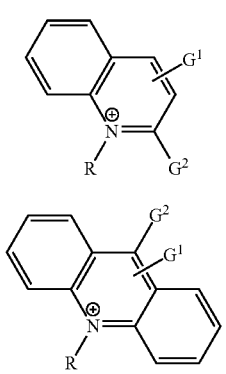

(IIIa)

(IIIb)

The following considerations and elaborations are equally applicable to the use of compounds of formulas I, Ia, Ib, III, IIIa, and/or as described above, as they are to compounds of formula II, IIa and IIb as described above, unless otherwise specified or conflicting with the definition of the compounds of formula I, Ia, Ib II, IIa, IIb, III, IIIa and IIb as described above.

Each of Ar$^1$, Ar$^2$ and Ar$^3$ may optionally be independently substituted with one or more substituents selected from the group consisting of -D, -T, —F, —Cl, —Br, —I, —NO$_2$, —CN, —R''', —OR''', —OC(O)R''', —SR''', —S(O)R''', —S(O)(O)R''' and —NR'''R'''', wherein —R''' and —R'''' are each independently selected from phenyl, tolyl and C$_1$-C$_{15}$ alkyl. Such substituents may affect the extent of conjugation of the Ar group in question, as well as its electron donating or electron withdrawing properties. In this manner, the reactivity and desorption/ablation properties of the compounds may be tuned. For example, Ar may be optionally substituted with one or more -Ph, —Cl or —Br groups.

Ar$^1$ may be selected from the group consisting of biphenyl, terphenyl, naphthalene, anthracene, phenanthrene, and pyrene. These aromatic groups have been proven to provide the compounds with adequate desorption/ablation properties for use as reactive matrices for desorption and/or laser ablation ionization spectrometry.

If -L- is a π-conjugating linker moiety, it may be selected from the group consisting of —O—, —S—, —NH—,

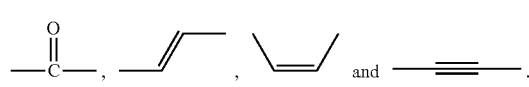

All of these linkers provide an adequate conjugation path between the Ar$^1$ group and the charged aromatic ring of the compound.

-L- may preferably be a bond, i.e. a direct bond between the Ar$^1$ group and the charged aromatic ring of the compound. This allows conjugation between the Ar$^1$ group and the charged aromatic ring of the compound without adding to the molecular weight of the compound.

-G$^1$ may be —H. -G$^1$ may be a phenyl group optionally substituted with one or more —Br substituents. This allows easy identification of molecules derivatized by the compound due to the characteristic isotope pattern and mass defect of the bromide substituent.

In some embodiments, the compound of formula I, Ia, Ib, II, IIa or IIb may be

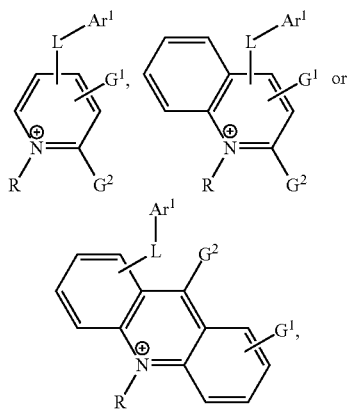

—R may optionally be labelled with one or more deuterium, tritium or carbon-13 atoms and may be selected from the group consisting of methyl, ethyl, n-propyl and n-butyl, and -G$^2$ may be selected from the group consisting of —F, —Cl, —Br and —I. Such compounds allow derivatization of nucleophilic target molecules by nucleophilic substitution at the alkylpyridine moiety.

In some embodiments

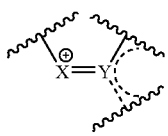

may be

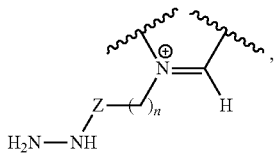

Z may be C=O, and n may be from 1 to 3. Such compounds allow derivatization of carbonyl-containing target molecules such as ketones or aldehydes, by formation of a hydrazone between the carbonyl of the target molecule and the hydrazine moiety of the compound.

In some embodiments

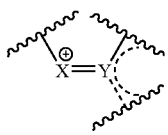

may be

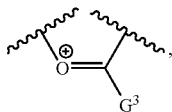

and -$G^3$ may be a phenyl group optionally substituted with one or more —Br substituents. Such compounds allow derivatization of primary amine-containing target molecules by nucleophilic attack at the pyrylium ring followed by ring-closure to provide a pyridinium derivative.

Further objects, advantages and novel features of the present invention will become apparent to one skilled in the art from the following detailed description.

BRIEF DESCRIPTION OF THE DRAWINGS

For a fuller understanding of the present invention and further objects and advantages of it, the detailed description set out below should be read together with the accompanying drawings, in which the same reference notations denote similar items in the various diagrams, and in which.

DETAILED DESCRIPTION

Figure 1A:
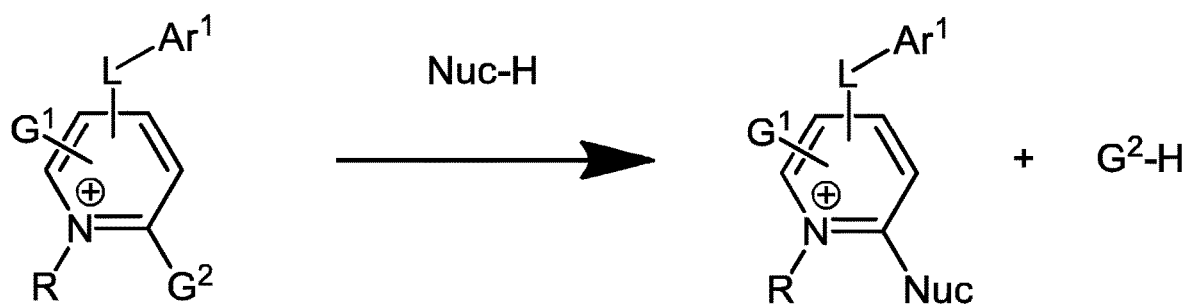
FIG. 1a schematically illustrates derivatization of a nucleophile using a 2-substituted N-alkylpyridinium-based reactive matrix FIG. 1b schematically illustrates derivatization of a carbonyl-containing compound using a hydrazine-based reactive matrix FIG. 1c schematically illustrates derivatization of a primary amine using a pyrylium-based reactive matrix FIG. 2a schematically illustrates a general synthetic method for producing 2-substituted N-alkylpyridinium-based reactive matrices FIG. 2b schematically illustrates a range of 2-substituted N-alkylpyridinium compounds that may be produced by the general synthetic method illustrated in FIG. 2a FIG. 3 schematically illustrates a general synthetic method for producing N-substituted pyridine reactive matrices having a hydrazine reactive moiety

The reactive matrices of the invention may facilitate the mass spectrometric analysis, e.g. MALDI-MS(I) and DESI-MS(I) analysis, of a broad range of compounds including pharmaceuticals and their metabolites, endogenous neurotransmitters, amino acids, metabolites, steroids, toxins as well as environmental pollutants, food additives, food ingredients and any other small molecules containing primary and secondary amines, phenolic hydroxide and carbonyl functional groups. The reactive matrices of the invention are important tools for rapid monitoring/molecular imaging of above-mentioned compounds in the following field for example: biology in general, medicine in general, neuroscience, cancer research, drug development, toxicology, environmental science and food chemistry.

The reactive matrices are applicable to a broad range of mass spectrometric (MS) and mass spectrometric imaging (MSI) techniques that utilize desorption and/or laser ablation. Such techniques include, but are not limited to:

Matrix-assisted laser desorption/ionization (MALDI-MS, MALDI-MSI);

Desorption electrospray ionization (DESI-MS, DESI-MSI);

Matrix-assisted laser desorption electrospray ionization (MALDESI-MS, MALDESI-MSI);

Nanospray desorption electrospray ionization (nano-DESI-MS, nano-DESI-MSI);

Secondary ion mass spectrometry (SIMS, SIMS-MSI);

Matrix-enhanced secondary ion mass spectrometry (ME-SIMS, ME-SIMS-MSI); and

Laser ablation electrospray ionization (LAESI-MS, LAESI-MSI).

The reactive matrices may also be utilizable in other forms of spectroscopy or mass spectrometry. For example, they may be used to label molecules with a chromophore prior to UV-spectroscopy or UV-imaging. They may also be used to provide a permanent charge ("charge-tagging") to molecules prior to mass spectrometry using electrospray ionization (ESI), and thus may be utilized in liquid extraction surface analysis (LESA) comprising either ESI or MALDI.

By reactive matrix it is meant a compound that may react with one or more target analyte molecules and facilitate the mass spectroscopic analysis of the target molecule(s). In some cases, use of the reactive matrix may completely avoid the need to use a further matrix to assist ionization. However, in some cases the reactive matrices may also be used together with a conventional non-reactive matrix in order to improve detection of the target molecule(s).

The reactive matrices disclosed herein incorporate at least two functional domains: a highly reactive domain that facilitates covalent analyte charge-tagging by derivatization; and a conjugated chromophore domain to promote laser-assisted desorption and/or ablation. However, in some cases wherein the reactive domain is part of a polycyclic ring system the reactive domain and conjugated chromophore domain may be integrated in one and the same ring system. The reactive matrices may also incorporate an identification domain; that is to say a suitable isotope or element having a distinctive isotope pattern and mass defect in order to facilitate mass-spectrometric identification of compounds that are derivatised by the reactive matrix.

Reactive Domain

The reactive domain of the reactive matrices may be an N-alkylpyridinium moiety having a suitable leaving group, an N-substituted pyridine having a hydrazine moiety, or a pyrylium moiety. All of these reactive domains have the advantage of providing a permanent positive charge to the analyte after derivatization, due to the presence after derivatization of an N-substituted pyridine moiety. This vastly increases the sensitivity of the analyte for positive ion mass spectrometry, especially for analytes that are otherwise difficult to protonate.

A reactive N-alkylpyridinium moiety having a suitable leaving group may selectively react with molecules comprising any one of a variety of common nucleophilic functional groups, including phenolic hydroxyl groups and primary and secondary amines. A reaction scheme demonstrating such derivatization reactions is shown in FIG. 1a. The reaction takes place without any need for extended incubation times. The leaving group ($G^2$ group) of the N-alkylpyridine may be any suitable leaving group for nucleophilic aromatic substitution. Such leaving groups include —F, —Cl, —Br, —I, —$NO_2$, —CN, —OR', —OC(O)R', —SR', —S(O)R', —S(O)(O)R' and —NR'R", wherein R' and R" are each independently phenyl or $C_1$-$C_{15}$ alkyl groups. The leaving group may suitably be positioned at the 2- or 4-positions of the pyridine ring, which are expected to be the most reactive positions for nucleophilic aromatic substitution ($S_NAr$). However, arrangement of the leaving group at the 3-position has been demonstrated to also provide sufficient reactivity, at least in some circumstances. The N-alkyl group is described below.

Figure 1B:
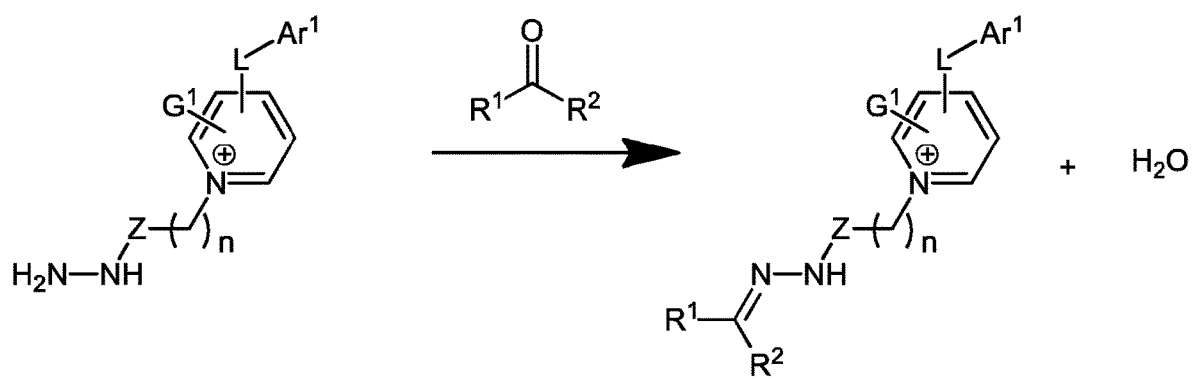

An N-substituted pyridine having a reactive hydrazine moiety may selectively react with any analytes having a carbonyl functionality, as shown in FIG. 1b. The reaction proceeds rapidly. The hydrazine moiety is bound by a linker to either the N-position or another position of the pyridine ring, such as the 2-position or 4-position. The linker may suitably be an alkyl chain, optionally comprising a carbonyl group closest to the hydrazine moiety. Alternatively, the linker may be a direct bond between the N-substituted pyridine and a nitrogen of the hydrazine moiety. If the hydrazine moiety is bound (via the linker) to a carbon of the pyridine ring, the N-position of the pyridine ring is alkylated in order to provide a permanently charged N-alkyl pyridine.

The N-alkyl group of the pyridine reactive domains may be any suitable group, such as a $C_1$-$C_{15}$ alkyl group. The N-alkyl group may be isotope-enriched, for example by having an abundance of $^2H$, $^3H$, $^{13}C$ or $^{14}C$ at a specific position. This may facilitate identification of the derivatized analytes by mass spectrometry. The N-alkyl group may be a chiral group allowing for stereoisomeric discrimination between analytes. Where the reactive domain is a 2-substituted N-alkylpyridinium, the N-alkyl group is preferably non-bulky in order to enable the nucleophilic substitution reaction at the 2-position of the pyridine ring. For example, the N-alkyl group may be a methyl group.

Figure 1C:
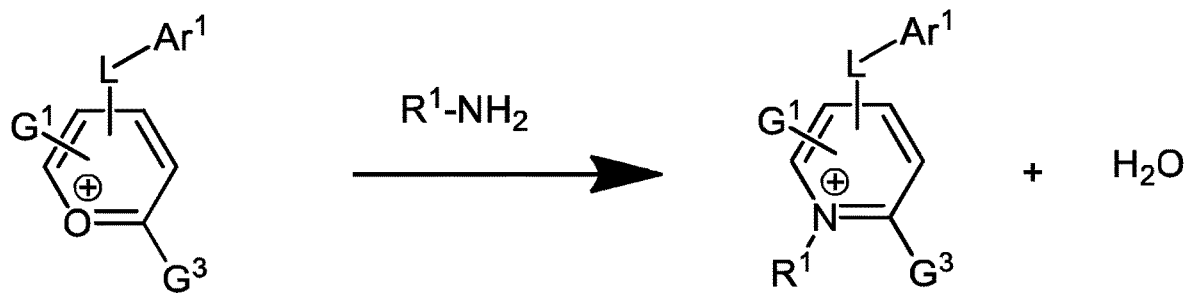

A pyrylium reactive moiety may selectively react with analytes having a primary amine functionality, resulting in an N-alkyl pyridine derivative as shown in FIG. 1c. This reaction may require substantial incubation times, depending on the exact nature of the pyrylium moiety and analyte.

Conjugated Chromophore Domain

The conjugated chromophore domain of the reactive matrix comprises an $Ar^1$ group selected from the group consisting of phenyl, biphenyl, terphenyl, $C_{10}$-$C_{30}$ polycyclic aromatic hydrocarbon and $C_4$-$C_{30}$ mono- or polycyclic heteroaryl. By polycyclic aromatic hydrocarbon it is meant a carbocyclic aromatic ring system comprising two or more fused rings. Suitable polycyclic aromatic hydrocarbons are for example listed as structures numbers 4-521 in NIST Special Publication 922 (revised June 2011) "Polycyclic Aromatic Hydrocarbon Structure Index", which is hereby incorporated by reference. The polycyclic aromatic hydrocarbon may for example be selected from the group consisting of naphthalene, fluorine, anthracene, phenanthrene, pyrene, tetracene, chrysene, perylene, corannulene, coronene and pyranthrene. By $C_4$-$C_{30}$ mono- or polycyclic heteroaryl, it is meant any heteroaryl ring system from 5-membered rings and upwards (i.e. furan, thiophene, pyrrole), including any heteroaryl analogues of the polyaromatic hydrocarbons as defined above. The heteroaryl rings may comprise any combination of carbon and heteroatoms, including but not limited to oxygen, sulfur and nitrogen atoms. The conjugated chromophore domain preferably exhibits strong optical absorption at the wavelength of the pulsed laser (typically 337 nm for nitrogen or 355 nm for Nd:YAG laser). For example, having a conjugated chromophore domain comprising an anthracene or substituted anthracene moiety provides reactive matrices having a suitable absorptivity, without having an excessive molar mass.

The $Ar^1$ group may be provided with one or more substituents in order to tailor the properties of the reactive matrix. Suitable substituents may for example include -D, -T, —F, —Cl, —Br, —I, —$NO_2$, —CN, —R''', —OR''', —OC(O)R''', —SR''', —S(O)R''', —S(O)(O)R''' and —NR'''R'''', wherein —R''' and —R'''' are each independently selected from phenyl, tolyl and $C_1$-$C_{15}$ alkyl.

By "conjugated chromophore domain" it is meant that the chromophore comprises a conjugated π-system, and not necessarily that the chromophore is conjugated with the reactive domain. However, in order to provide suitable absorptivity the conjugated system may extend into the pyridine/pyrylium ring of the derivatized analyte. This is particularly preferable in cases where the $Ar^1$ group by itself does not have a sufficiently extended π-system in order to absorb at the wavelengths mentioned above. This is achieved by connecting the $Ar^1$ group to the pyridine or pyrylium moiety using a π-conjugating linker moiety. By π-conjugating linker moiety it is meant a moiety providing an uninterrupted π-conjugation path between the $Ar^1$ group and the pyridine/pyrylium moiety, i.e. a direct bond between the $Ar^1$ group and the pyridine/pyrylium moiety, or a moiety comprising only sp and/or $sp^2$ hybridized atoms in a path directly connecting the $Ar^1$ group to the pyridine/pyrylium moiety. Such a moiety may as noted above be a direct bond between the $Ar^1$ group and the pyridine/pyrylium moiety, or it may be a moiety selected from the group consisting of —O—, —S—, —NH—,

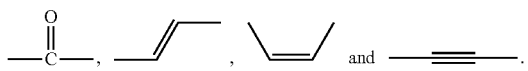

The π-conjugating linker moiety may comprise pendant groups comprising sp³ hybridized atoms, wherein by pendant groups it is meant groups not directly incorporated in the conjugation path between the Ar¹ group and the pyridine/pyrylium moiety. For example, the π-conjugating linker moiety may comprise chiral pendant groups in order to facilitate stereoisomeric discrimination between analytes. The π-conjugating linker moiety may also allow for axial chirality (atropisomerism) due to restricted rotation of the Ar¹ group relative to the pyridine/pyrylium moiety. This may especially be the case where the π-conjugating linker moiety is a direct bond. However, if the Ar¹ group by itself has suitable absorption, it is not necessarily advantageous to extend the conjugated system into the pyridine/pyrylium ring, and in such cases a non-conjugating linker, such as an alkyl chain or any other chain comprising sp³ hybridized carbon atoms, may be used to connect the pyridine/pyrylium ring to the Ar¹ group.

A suitable G¹ group may be chosen to tailor the chromophore and reactive properties of the reactive matrix. G¹ may be selected from —H, -Me or —Ar², wherein —Ar² is optionally substituted and is selected from the group consisting of phenyl, biphenyl, terphenyl, $C_{10}$-$C_{30}$ polycyclic aromatic hydrocarbon, and $C_4$-$C_{30}$ mono- or polycyclic heteroaryl. If G¹ is an aryl (Ar²) group, this may further extend the π-conjugation into the G¹ group, thus altering the absorptivity of the reactive matrix. The reactive and chromophore properties of the reactive matrix may be further tuned by providing the —Ar² group with one or more substituents when G¹ is an Ar² group. Suitable substituents may include -D, -T, —F, —Cl, —Br, —I, —NO₂, —CN, —R', —OR''', —OC(O)R''', —SR''', —S(O)R''', —S(O)(O)R''' and —NR'''R'''', wherein —R''' and —R'''' are each independently selected from phenyl, tolyl and $C_1$-$C_{15}$ alkyl.

Where the reactive domain is a pyrylium moiety, a suitable G³ group may be chosen to tailor the chromophore and reactive properties of the reactive matrix. The G³ group may independently be selected from the same substituents as for the G¹, as described above.

Integrated Reactive Domain and Conjugated Chromophore Domain

In some cases wherein the reactive domain is part of a polycyclic ring system, a separate conjugated chromophore domain may not be required due to the reactive domain by itself having sufficiently good chromophore properties, i.e. the reactive domain and conjugated chromophore domain may be integrated into one and the same ring system. This for example may be the case where the reactive domain is a fused N-alkylpyridinium moiety, such as an N-alkylacridine moiety or an N-alkylquinoline moiety. Such integrated systems may provide improved atom economy.

Identification Domain

The reactive matrices may be provided with an identification domain that facilitates mass spectrometric identification of analytes charge-tagged with the reactive matrix. This may for example be achieved by providing a chlorine or bromine substituent on the reactive matrix, since these atoms provide a distinctive mass spectroscopic isotope pattern and mass defects.

Alternatively, the reactive matrix may be isotope enriched by substitution with deuterium, tritium or an alkyl or aryl group enriched with a carbon isotope such as ¹³C or ¹⁴C. By labelled, isotope-enriched or substituted with a particular isotope, it is meant that the occurrence of a particular isotope (e.g. ²H, ³H, ¹³C or ¹⁴C) at a certain position in the molecule vastly exceeds the naturally occurring abundance at that position. For example, the ratio of the "identification" isotope (e.g. ²H, ³H, ¹³C or ¹⁴C) to the most abundant naturally occurring isotope (e.g. 1H or ¹²C) at the relevant position may be at least 1:10, such as at least 1:1 or at least 10:1.

The reactive matrices possess a permanent positive charge and thus may be prepared as salts with one or more anionic counterions. Such salts may for example comprise one or more anions selected from the non-exhaustive group consisting of chloride, bromide, iodide, toslylate, mesylate, tetrafluoroborate, perfluorobutanesulfonate, benzenesulfonate, hexafluorophosphate and triflate.

Use of the Reactive Matrices in Desorption and/or Laser Ablation Ionization Mass Spectrometry When preparing a sample for mass spectrometric analysis or imaging, the reactive matrix substances in most cases do not need any incubation with the sample. The reaction occurs at the same time when the reagent is added/spotted/sprayed to/over the sample without any need for cooling or heating. Depending on the nature of the reactive domain, the reactive matrices target substances with primary amine, secondary amine, phenolic hydroxide, aldehyde or ketone functional groups. All of the reactive matrices carry a permanent positive charge after reacting with the functional group of the analyte. This allows for high sensitivity detection and analysis of the derivatized analytes.

EXAMPLES

Figure 2A:
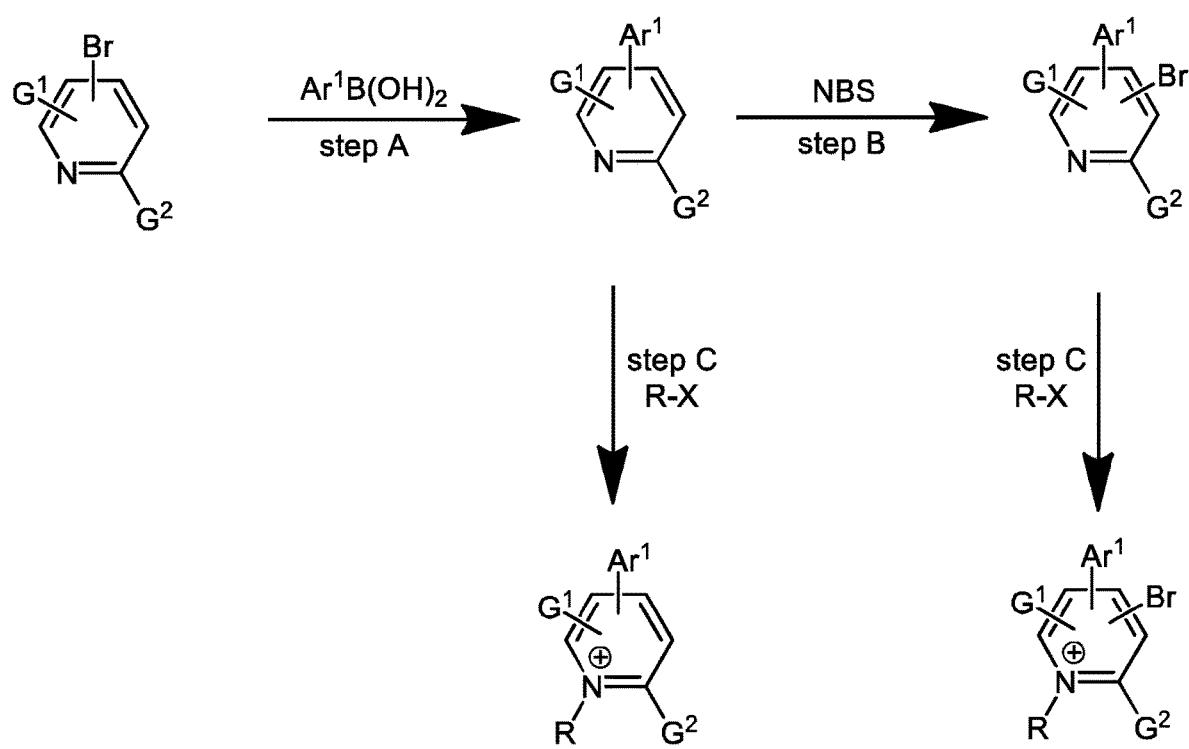
Figure 2B:
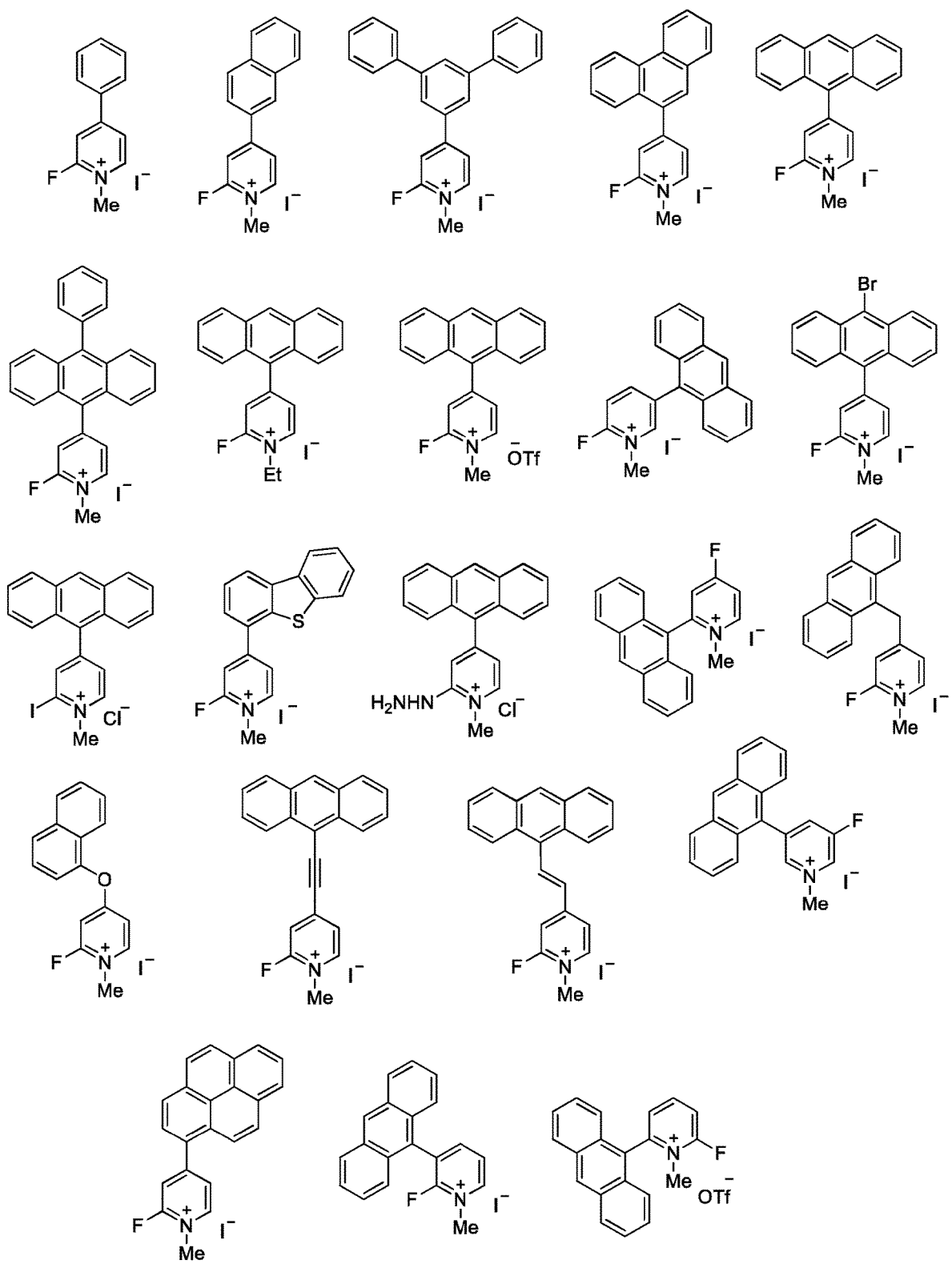

Example 1: Synthesis of 2-Substituted N-alkylpyridinium Reactive Matrices 2-substituted N-alkylpyridinium reactive matrices are synthesised by a modular synthetic route as schematically illustrated in FIG. 2a. The two domains (chromophore and reactive domain) are fused using a Suzuki-Miyara cross-coupling reaction in step A. Thus, treatment of the appropriate 2-substituted bromopyridine derivative with a range of aryl boronic acids under palladium-catalysis afforded the precursor compounds in moderate to excellent yield. These precursors may in an optional step B be regioselectively brominated with N-bromosuccinimide to introduce an identification domain. The precursors are then subsequently alkylated in a step C under thermal conditions to afford afforded the desired reactive matrix. A selection of reactive matrices produced by this method are shown in FIG. 2b. Notably the final compounds were readily isolated by simple filtration, which negated the need for a potentially problematic purification step. The compounds were found to be stable upon storage under vacuum for months, however they degrade slowly when stored in solution.

General Procedure A for Synthesis of 2-fluoro pyridines Exemplified by 2-fluoro-4-phenylpyridine All reagents were purchased at the highest commercial quality and used without further purification. Yields refer to isolated, homogenous and spectroscopically pure material, unless otherwise stated. Crude reaction mixtures were purified by silica gel chromatography (E. Merck silica gel, particle size 0.043-0.063 mm). Thin layer chromatography was carried out using E. Merck silica plates (60F-254) with UV light (254 nm) as the visualization agent. ¹H NMR spectra were recorded at 400 MHz and ¹³C{¹H} NMR spectra at 100 MHz. The chemical shifts for $^1$H NMR and $^{13}$C{$^1$H} NMR spectra were referenced to tetramethylsilane via residual solvent signals ($^1$H, CDCl$_3$ at 7.26 ppm, Acetone-d$_6$ at 2.05 ppm, CD$_3$CN at 1.95 ppm; $^{13}$C, CDCl$_3$ at 77.16 ppm, Acetone-d$_6$ at 29.9 ppm, CD$_3$CN at 1.39 ppm). LC/MS analysis was performed on an instrument equipped with a C18 column (50×3.0 mm, particle size 2.6 μm, pore size 100 Å) an electrospray ionization source and a single quadrupole detector. Accurate mass values were determined on a mass spectrometer equipped with an electrospray or MALDI ion source and TOF or FTICR analyzer.

To a stirred solution of 4-bromo-2-fluoropyridine (528 mg, 3 mmol), phenylboronic acid (399 mg, 3.3 mmol), Pd(PPh$_3$)$_4$ (69 mg, 0.06 mmol) in toluene/ethanol (4:1, 25 ml) was added a solution of Na$_2$CO$_3$ (1.27 g, 12 mmol) in water (10 ml). The resulting yellow solution was stirred at 80° C. for 2 hours, during which time the solution turned black. After cooling to ambient temperature the reaction mixture was extracted with EtOAc (3×50 ml). The combined organic layers were the washed with brine (50 ml), dried over MgSO$_4$, filtered and concentrated in vacuo. The crude product was purified by hot filtration from MeOH followed by silica gel chromatography (5% EtOAc in n-pentane) to the title compound as a light yellow solid (490 mg, 2.8 mmol, 94%).

Optional General Procedure B for the Bromination of 2-fluoropyridines Exemplified by 4-(10-Bromoanthracen-9-yl)-2-fluoropyridine To a stirred solution of 4-(anthracen-9-yl)-2-fluoropyridine (715 mg, 2.75 mmol) in CHCl$_3$ (35 ml) was added N-bromosuccinimide (1.08 g, 6.07 mmol) and the resulting solution was refluxed for 48 h. After cooling to room temperature, the mixture diluted with water (25 ml) and extracted with CH$_2$Cl$_2$ (3×25 ml). The combined organic layers were dried over MgSO4, filtered and concentrated in vacuo. Purification by flash column chromatography (SiO$_2$, EtOAc:toluene:pentane 5:15:80 (v/v/v)) provided the title compound as a yellow solid (784 mg, 85%).

General Procedure C for the Preparation of N-alkyl arylfluoropyridium salts Exemplified by 2-fluoro-1-methyl-4-phenylpyridin-1-ium iodide 2-fluoro-4-phenylpyridine (200 mg, 1.15 mmol) was dissolved in MeI (2 mL) and the resulting solution was heated in a sealed vial at 60° C. for 72 h. The resulting precipitate was collected by filtration, washed with diethylether (3×5 ml) and acetone (2 ml) and dried under vacuum to afford the title compound as a yellow solid (273 mg, 0.87 mmol, 75%). These compounds react readily with any nucleophilic solvent and should be handled accordingly.

The following compounds exemplify reactive matrices that may be prepared by the general methods described above:

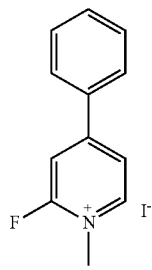

2-Fluoro-1-methyl-4-phenylpyridin-1-ium iodide (2)

Prepared following the general procedures A and C, starting from 2-fluoro-4-bromopyridine. $^1$H NMR (400 MHz, CDCl$_3$/CD$_6$CO): δ 9.25-9.11 (m, 1H), 8.42-8.33 (m, 2H), 8.11-8.00 (m, 2H), 7.72-7.57 (m, 3H), 4.48 (d, J=3.7 Hz, 3H).

$^{13}$C NMR (100 MHz, CDCl$_3$/CD$_6$CO): δ 161.7 (d, J=11.4 Hz), 144.6 (d, J=7.2 Hz), 132.8, 129.7, 128.1, 121.1 (d, J=3.0 Hz), 110.2 (d, J=21.5 Hz), 41.2 (d, J=5.2 Hz).

Accurate mass (MALDI, m/z): calc'd for C$_{12}$H$_{11}$FN ([M$^+$]): 188.0870, found m/z 188.0877.

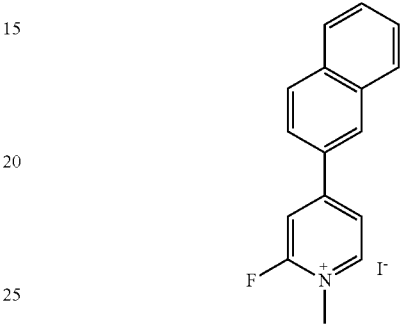

2-Fluoro-1-methyl-4-(naphthalen-2-yl)pyridin-1-ium iodide (3)

Prepared following the general procedures A and C, starting from 2-fluoro-4-bromopyridine. $^1$H NMR (400 MHz, CDCl$_3$/CD$_6$CO): δ 8.90 (dd, J=6.7, 4.9 Hz, 1H), 8.62 (d, J=2.0 Hz, 1H), 8.36 (dd, J=6.7, 2.1 Hz, 1H), 8.24 (dd, J=5.7, 2.1 Hz, 1H), 8-18-8.14 (m, 2H), 8.10-8.02 (m, 1H), 8.00 (dt, J=8.7, 2.2 Hz, 1H), 7.82-7.66 (m, 2H), 4.36 (d, J=3.5 Hz, 3H).

$^{13}$C NMR (100 MHz, CDCl$_3$/CD$_6$CO): δ 161.6 (d, J=11.7 Hz), 143.6 (d, J=6.8 Hz), 135.2, 133.0, 130.0, 129.9, 129.4, 128.7, 127.9, 127.7, 123.6, 121.4 (d, J=2.8), 111.3 (d, J=21.9 Hz), 41.5 (d, J=5.0 Hz).

Accurate mass (MALDI, m/z): calc'd for C$_{16}$H$_{13}$FN ([M$^+$]): 238.1027, found m/z 238.1028.

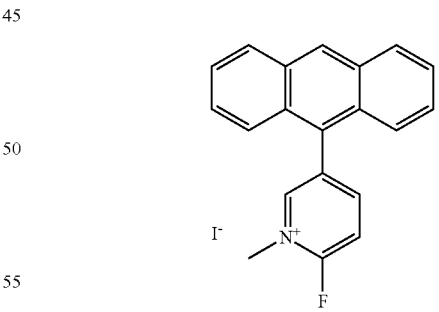

5-(Anthracen-9-yl)-2-fluoro-1-methylpyridin-1-ium iodide (4)

Prepared following the general procedures A and C, starting from 2-fluoro-4-bromopyridine. $^1$H NMR (400 MHz, CDCl$_3$/CD$_6$CO): δ 8.77 (s, 1H), 8.64 (ddd, J=8.5, 5.6, 2.3 Hz, 1H), 8.59 (dd, J=4.2, 2.2 Hz, 1H), 8.18 (dt, J=8.2, 1.3 Hz, 2H), 8.05 (dd, J=8.7, 4.0 Hz, 1H), 7.61-7.52 (m, 6H), 4.29 (d, J=3.8 Hz, 3H).

¹³C NMR (100 MHz, CDCl₃/CD₆CO): δ 154.4 (d, J=11.4 Hz), 145.8 (d, J=6.8 Hz), 136.0 (d, J=3.8 Hz), 137.6, 130.8, 130.4, 129.5, 127.9, 126.6, 126.4, 125.4, 115.5 (d, J=20.3 Hz), 42.9 (d, J=5.1 Hz).

Accurate mass (MALDI, m/z): calc'd for C₂₀H₁₅FN ([M⁺]): 288.1183, found m/z 288.1179.

130.7, 129.6, 128.9, 127.9, 126.1, 122.2 (d, J=3.1 Hz), 111.4 (d, J=20.3 Hz), 41.9 (d, J=5.1 Hz).

Accurate mass (MALDI, m/z): calc'd for C₂₄H₂₀FN ([M⁺]): 340.1496, found m/z 340.1496.

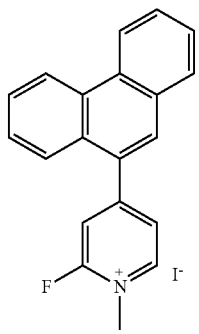

2-Fluoro-1-methyl-4-(phenanthren-9-yl)pyridin-1-ium iodide (5)

Prepared following the general procedures A and C, starting from 2-fluoro-4-bromopyridine.

¹H NMR (400 MHz, CDCl₃/CD₆CO): δ 8.85-8.79 (m, 1H), 8.78-8.69 (m, 2H), 8.05-8.02 (m, 2H), 8.00 (dd, J=5.0, 1.9 Hz, 1H), 7.96 (s, 1H), 7.88 (dd, J=8.2, 1.2 Hz, 1H), 7.84-7.77 (m, 2H), 7.74-7.66 (m, 2H), 4.30 (d, J=3.6 Hz, 3H).

¹³C NMR (100 MHz, CDCl₃/CD₆CO): δ 163.4 (d, J=11.5 Hz), 143.9 (d, J=6.7 Hz), 132.3 (d, J=1.9 Hz), 131.7, 131.2, 130.9, 130.8, 130.1, 129.7, 128.6, 128.5, 128.4, 128.3, 125.8 (d, J=3.2 Hz), 125.6, 124.3, 123.5, 115.5 (d, J=20.5 Hz), 42.3 (d, J=5.0 Hz).

Accurate mass (MALDI, m/z): calc'd for C₂₀H₁₆FN ([M⁺]): 288.1183 found m/z 288.1177.

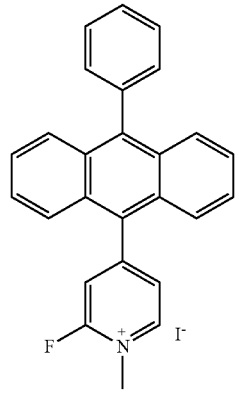

2-Fluoro-1-methyl-4-(10-phenylanthracen-9-yl)pyridin-1-ium iodide (7)

Prepared following the general procedures A and C, starting from 2-fluoro-4-bromopyridine. ¹H NMR (400 MHz, CDCl₃/CD₆CO): δ 8.87-8.84 (m, 1H), 7.98-7.94 (m, 2H), 7.70 (dd, J=8.7, 1.4, 0.8 Hz, 2H), 7.68-7.56 (m, 5H), 7.55-7.51 (m, 2H), 7.48-7.39 (m, 4H), 4.38 (d, J=3.7 Hz, 3H).

¹³C NMR (100 MHz, CDCl₃/CD₆CO): δ 164.1 (d, J=11.5 Hz), 144.8 (d, J=6.8 Hz), 141.3, 138.3, 131.3, 130.0, 129.3, 129.2, 128.9, 128.7, 128.0 (d, J=3.5 Hz), 127.9, 127.8, 126.4, 125.2, 117.0 (d, J=20.9 Hz), 42.4 (d, J=5.1 Hz).

Accurate mass (MALDI, m/z): calc'd for C₂₆H₁₉FN ([M⁺]): 364.1496, found m/z 364.1486.

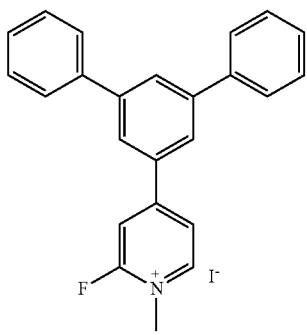

4-([1,1':3',1''-Terphenyl]-5'-yl)-2-fluoro-1-methylpyridin-1-ium iodide (6)

Prepared following the general procedures A and C, starting from 2-fluoro-4-bromopyridine. ¹H NMR (400 MHz, CDCl₃/CD₆CO): δ 8.71-8.68 (m, 1H), 8.31 (dd, J=6.7, 2.0 Hz, 1H), 8.26 (dd, J=5.7, 2.0 Hz, 1H), 8.13-8.10 (m, 1H), 8.10 (d, J=1.7 Hz, 21H), 7.80-7.76 (m, 4H), 7.55-7.49 (m, 4H), 7.49-7.41 (m, 2H), 4.23 (d, J=3.6 Hz, 3H).

¹³C NMR (100 MHz, CDCl₃/CD₆CO): δ 162.0 (d, J=11.5 Hz), 144.1 (d, J=7.0 Hz), 143.8, 139.9, 134.7 (d, J=2.2 Hz),

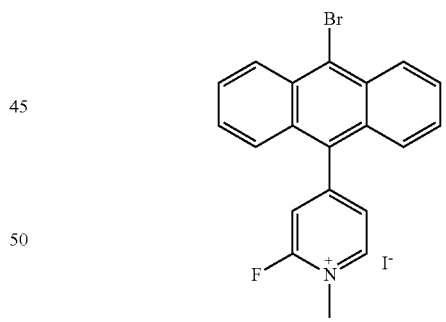

4-(10-Bromoanthracen-9-yl)-2-fluoro-1-methylpyridin-1-ium (8)

Prepared following the general procedures A, B and C, starting from 2-fluoro-4-bromopyridine.

¹H NMR (400 MHz, CDCl₃/CD₆CO): δ 9.01 (t, J=5.6 Hz, 1H), 8.53 (dd, J=8.9, 1.0 Hz, 2H), 7.78 (dd, J=6.4, 1.7 Hz, 1H), 7.69 (dd, J=4.3, 1.7 Hz, 1H), 7.56 (ddd, J=9.0, 6.4, 1.2 Hz, 2H), 7.50 (dd, J=8.7, 1.1 Hz, 2H), 7.42 (ddd, J=8.8, 6.4, 1.1 Hz, 2H), 4.36 (d, J=3.7 Hz, 3H).

¹³C NMR (100 MHz, CDCl₃/CD₆CO): δ 161.0 (d, J=11.5 Hz), 143.7 (d, J=6.5 Hz), 129.2, 128.7 (d, J=1.6 Hz), 128.6, 127.5, 127.2, 127.1, 126.5 (d, J=3.4 Hz), 125.4, 124.6, 124.5, 116.6 (d, J=16.9 Hz), 41.40 (d, J=5.0 Hz).

Accurate mass (MALDI, m/z): calc'd for $C_{20}H_{14}BrFN$ ([M$^+$]): 366.0288, found m/z 366.0284.

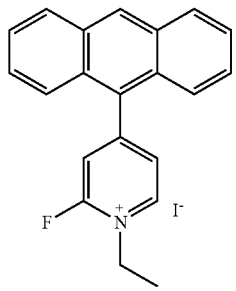

4-(Anthracen-9-yl)-2-fluoro-1-ethylpyridin-1-ium (9)

Prepared following the general procedures A and C, starting from 2-fluoro-4-bromopyridine and using ethyl iodide as the alkylating agent. $^1$H NMR (400 MHz, CDCl$_3$/CD$_6$CO): 9.32 (dd, J=6.4, 4.8 Hz, 1H), 8.67 (s, 1H), 8.12-8.07 (m, 2H), 7.96 (dd, J=6.4, 1.7 Hz, 1H), 7.79 (dd, J=4.8, 1.7 Hz, 1H), 7.64-7.61 (m, 2H), 7.55-7.45 (m, 4H), 4.92 (qd, J=7.4, 2.4 Hz, 2H), 1.81 (t, J=7.3 Hz, 3H).

$^{13}$C NMR (100 MHz, CDCl$_3$/CD$_6$CO): δ 163.3 (d, J=11.3 Hz), 143.5 (d, J=6.5 Hz), 130.9, 130.5, 129.0, 128.7, 128.1 (d, J=1.7 Hz), 127.9 (d, J=3.0 Hz), 127.8, 125.9, 124.4, 117.3 (d, J=19.5 Hz), 51.8 (d, J=4.3 Hz), 14.8 (d, J=1.0 Hz).

Accurate mass (MALDI, m/z): calc'd for $C_{21}H_{17}FN$ ([M$^+$]): 302.1340, found m/z 302.1334.

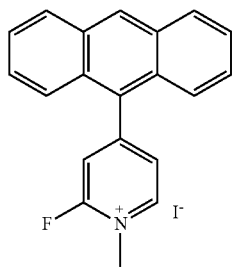

4-(Anthracen-9-yl)-2-fluoro-1-methylpyridin-1-ium iodide (10)

Prepared following the general procedures A and C, starting from 2-fluoro-4-bromopyridine. $^1$H NMR (400 MHz, CDCl$_3$/CD$_6$CO): δ 8.89 (t, J=5.5 Hz, 1H), 8.72 (s, 1H), 8.15-8.13 (m, 2H), 7.92-7.90 (m, 1H), 7.87-7.85 (m, 1H), 7.61-7.46 (m, 6H), 4.39 (d, J=3.7 Hz, 3H).

$^{13}$C NMR (100 MHz, CDCl$_3$/CD$_6$CO): δ 163.7 (d, J=11.4 Hz), 144.6 (d, J=6.8 Hz), 131.2, 130.7, 129.4, 129.1, 128.0, 127.7 (d, J=3.2 Hz), 126.2, 124.8, 117.6 (d, J=20.9 Hz), 42.4 (d, J=5.1 Hz).

Accurate mass (MALDI, m/z): calc'd for $C_{20}H_{15}FN$ ([M$^+$]): 288.1183, found m/z 288.1184.

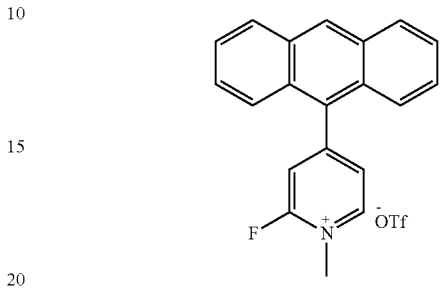

4-(Anthracen-9-yl)-2-fluoro-1-methylpyridin-1-ium trifluoromethylsulfonate (11)

Prepared following the general procedures A and C, starting from 2-fluoro-4-bromopyridine and using methyl triflate as the methylating agent.

$^1$H NMR (400 MHz, CDCl$_3$/CD$_6$CO): δ 8.81-8.73 (m, 1H), 8.72 (s, 1H), 8.15-8.02 (m, 2H), 7.84 (dd, J=6.4, 1.7 Hz, 1H), 7.78 (dd, J=4.6, 1.7 Hz, 1H), 7.62-7.43 (m, 6H), 4.38 (d, J=3.7 Hz, 3H).

$^{13}$C NMR (100 MHz, CDCl$_3$/CD$_6$CO): δ 163.7 (d, J=11.4 Hz), 144.6 (d, J=6.8 Hz), 131.0, 130.6, 129.1, 128.9, 128.4, (d, J=3.2 Hz), 126.1, 124.4, 117.2, 42.1 (d, J=5.1 Hz).

Accurate mass (MALDI, m/z): calc'd for $C_{20}H_{15}FN$ ([M$^+$]): 288.1183, found m/z 288.1176.

Example 2: Determination of MALDI-MS Sensitivity of Derivatised Model Compounds

To evaluate and compare the efficiency of the synthesized substances as reactive matrices for high sensitivity MALDI-MSI analysis, small molecules with different functional groups were spotted on the cortical area of a rat control brain tissue section. On the same tissue sections, rectangular regions of interest were selected in the striatal area of each brain. MALDI-MSI analysis were performed for all model substances as well as the selected striatal area with different synthesized reactive matrices. Signal to noise (S/N) values for all derivatized compounds were calculated using an in-house developed software (Kallback, P., Nilsson, A., Shariatgorji, M. & Andren, P. E. msIQuant—Quantitation Software for Mass Spectrometry Imaging Enabling Fast Access, Visualization, and Analysis of Large Data Sets. Anal Chem 88, 4346-4353 (2016)). The results are shown in Table 1 below.

TABLE 1

| No. | Name | Mol. wt. | Added mass to target molecule | Signal to noise values for detection of derivatized compounds | | | | |
|---|---|---|---|---|---|---|---|---|
| | | | | $D_4$-DA single/double | Endogenous DA | PEA | EPI | HD |
| 1 | 2-fluoro-1-methylpyridin-1- | 112.05570 | 92.04948 | ND | ND | ND | ND | ND |

TABLE 1-continued

| No. | Name | Mol. wt. | Added mass to target molecule | D$_4$-DA single/ double | Endogenous DA | PEA | EPI | HD |
|---|---|---|---|---|---|---|---|---|
| | ium P-toluenesulfonate | | | | | | | |
| 2 | 2-fluoro-1-methyl-4-phenylpyridin-1-ium iodide | 188.08700 | 168.08078 | ND | ND | ND | ND | ND |
| 3 | 2-fluoro-1-methyl-4-(naphthalen-2-yl)pyridin-1-ium iodide | 238.10265 | 218.09643 | 14/ND | 2/ND | 9 | 61/ND | 442 |
| 4 | 5-(anthracen-9-yl)-2-fluoro-1-methylpyridin-1-ium iodide | 288.11830 | 268.11208 | 254/332 | 14/30 | 17 | 156/213 | 637 |
| 5 | 2-fluoro-1-methyl-4-(phenanthren-9-yl)pyridin-1-ium iodide | 288.11830 | 268.11208 | 20/204 | 2/26 | 6 | 29/365 | 348 |
| 6 | 4-([1,1':3',1''-Terphenyl]-5'-yl)-2-fluoro-1-methylpyridin-1-ium iodide | 340.14960 | 320.14338 | 152/341 | 25/105 | 17 | 93/3 | 200 |
| 7 | 2-fluoro-1-methyl-4-(10-phenylanthracen-9-yl)pyridin-1-ium iodide | 364.14960 | 344.14338 | 14/ND | 2/ND | 16.0 | 19/ND | 178 |
| 8 | 4-(10-bromoanthracen-9-yl)-2-fluoro-1-methylpyridin-1-ium iodide | 366.02882 | 346.02259 | 28/18 | 6/5 | 27 | 72/35 | 433 |
| 9 | 4-(Anthracen-9-yl)-2-fluoro-1-ethylpyridin-1-ium iodide | 302.13395 | 282.12773 | 72 | 605 | 17/247 | 75/493 | 959 |
| 10 | 4-(Anthracen-9-yl)-2-fluoro-1-methylpyridin-1-ium iodide | 288.11830 | 268.11208 | 115/522 | 16/342 | 79 | 149/827 | 802 |
| 11 | 4-(Anthracen-9-yl)-2-fluoro-1-methylpyridin-1-ium trifluoromethyl sulfonate | 288.11830 | 268.11208 | 204/117 | 19/18 | 111 | 70/46 | 377 |
| 12 | 2,5-Dihydroxy benzoic acid (DHB) | 154.027 | 1.007 | 5.4* | ND | 8.2 | 21.7* | 22 |
| 13 | α-Cyano-4-hydroxycinnamic acid (CHCA) | 189.042 | 1.007 | ND | ND | ND | ND | 1.2 |

ND = not detected (S/N ratio < 3)
* = 10 times higher concentration of analyte used
DA = dopamine;
PEA = Phenethylamine;
EPI = epinephrine;
HD = hordenine It can be concluded from the S/N values that iodide salts of the ethylated and methylated 4-(Anthracen-9-yl)-2-fluoro-1-alkylpyridin-1-ium (entries 9 and 10) produced the best S/N values for the tested model compounds. The traditional non-reactive matrices CHCA and DHB (entries 13 and 12 respectively), which are the most widely used positive ion mode non-reactive/non-selective MALDI-MS assisting matrices for small molecules, were compared with the newly synthesized reactive matrices. The data presented in table 1 show a significant enhancement of sensitivity ranging from at least 10 times for the detection of phenethylamine to about 500 times for the analysis of dopamine when using the synthesized reactive matrices, as compared to the traditional non-reactive matrices.

Figure 3:
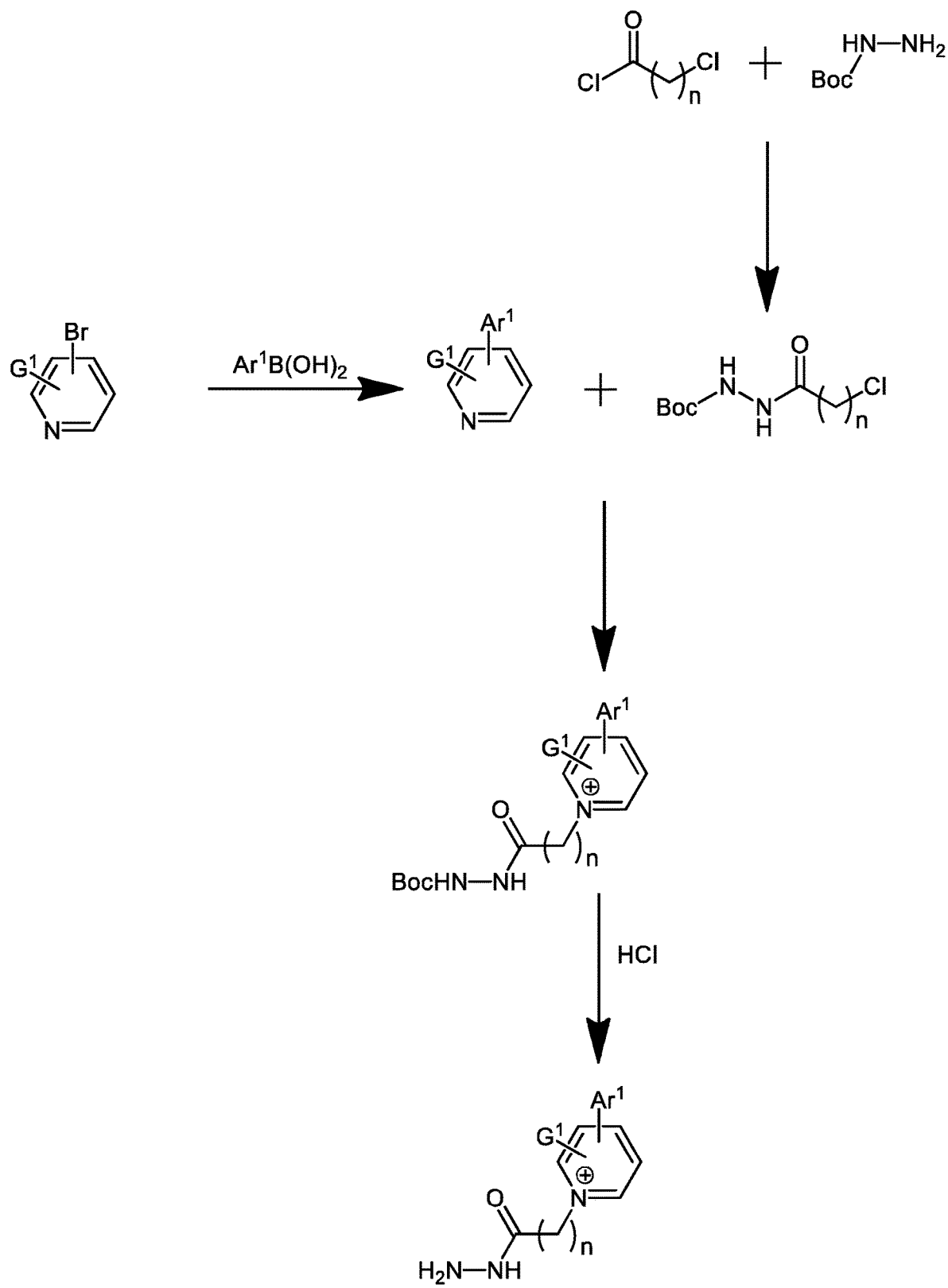

Example 3: Synthesis of 4-(anthracen-9-yl)-1-(2-hydrazinyl-2-oxoethyl)pyridin-1-ium A general method for the synthesis of reactive matrices having a reactive hydrazine moiety bound at the N-pyridine position is shown in FIG. 3. The procedure is exemplified by the synthesis of 4-(anthracen-9-yl)-1-(2-hydrazinyl-2-oxoethyl)pyridin-1-ium as described below. Note however that Boc-hydrazine may be reacted with acyl halides or alkyl halides other than chloroacetyl chloride, thus enabling the provision of reactive matrices having a variety of alkyl or oxo-alkyl chains binding the hydrazine moiety to the nitrogen of the pyridine ring.

tert-butyl 2-(2-chloroacetyl)hydrazine-1-carboxylate

To a stirred and cooled (0° C.) solution of tert-butyl hydrazinecarboxylate (1.98 g, 15 mmol, 2 equiv) in DCM (20 ml) and pyridine (0.79 g, 10 mmol, 1.5 equiv) was added chloro acetyl chloride (1.12 g, 10 mmol, 1.5 equiv) in DCM (5 ml). The reaction mixture was stirred over a period of 6 h and washed three times with diluted HCl (50 ml). The organic phase was dried over $Na_2SO_4$. The solvent was removed under reduced pressure, to yield the title compound as a clear oil (1.16 g, 55%).

4-(anthracen-9-yl)-1-(2-(2-(tert-butoxycarbonyl)hydrazinyl)-2-oxoethyl)pyridine-1-ium chloride A solution of 4-(anthracen-9-yl)pyridine (0.33 g, 1.29 mmol, 1 equiv., produced by general method A above), tert-butyl 2-(2 chloroacetyl)hydraxine-1-carboxylate (0.54 g, 2.58 mmol, 2 equiv) in chloroform (2 ml) was heated at 120° C. for 30 minutes. The reaction mixture was left to crystalize and the solid product was filtered and washed with ethyl acetate. It was purified with vapor diffusion crystallization (EtOH and diethyl ether). Yield of the yellow product (0.44 g, 81%).

4-(anthracen-9-yl)-1-(2-hydrazinyl-2-oxoethyl)pyridin-1-ium

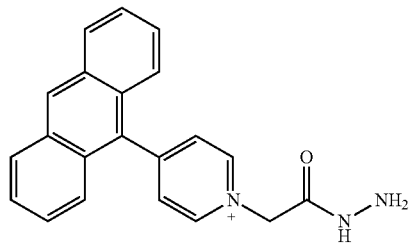

To a stirred solution of 4-(anthracen-9-yl)-1-(2-(2-(tert-butoxycarbonyl)hydrazinyl)-2-oxoethyl)pyridine-1-ium chloride (50 mg, 0.12 mmol) in 1 ml 10% MeOH in DCM was added 1 ml of 4M HCl in 1,4-dioxane solution drop wise under nitrogen. The reaction mixture was stirred over night at room temperature under nitrogen. The precipitated form was filtered, washed with EtOAc and dried. Yield of yellow powder (36 mg, 94%). $^1$H NMR (400 MHz, DMSO-$d_6$) δ 9.35 (d, J=6.0 Hz, 2H), 8.90 (s, 1H), 8.42 (d, J=6.3 Hz, 2H), 8.25 (dd, J=8.3, 1.3 Hz, 2H), 7.60 (m, 2H) 7.55, 7.41 (d, 2H), 5.88 (s, 2H). $^{13}$C NMR (101 MHz, DMSO-$d_6$) δ 164.5, 157.2, 147.0, 131.0, 130.8, 130.3, 129.8, 129.4, 128.7, 127.9, 126.3, 124.9, 60.1.

Figure 4:
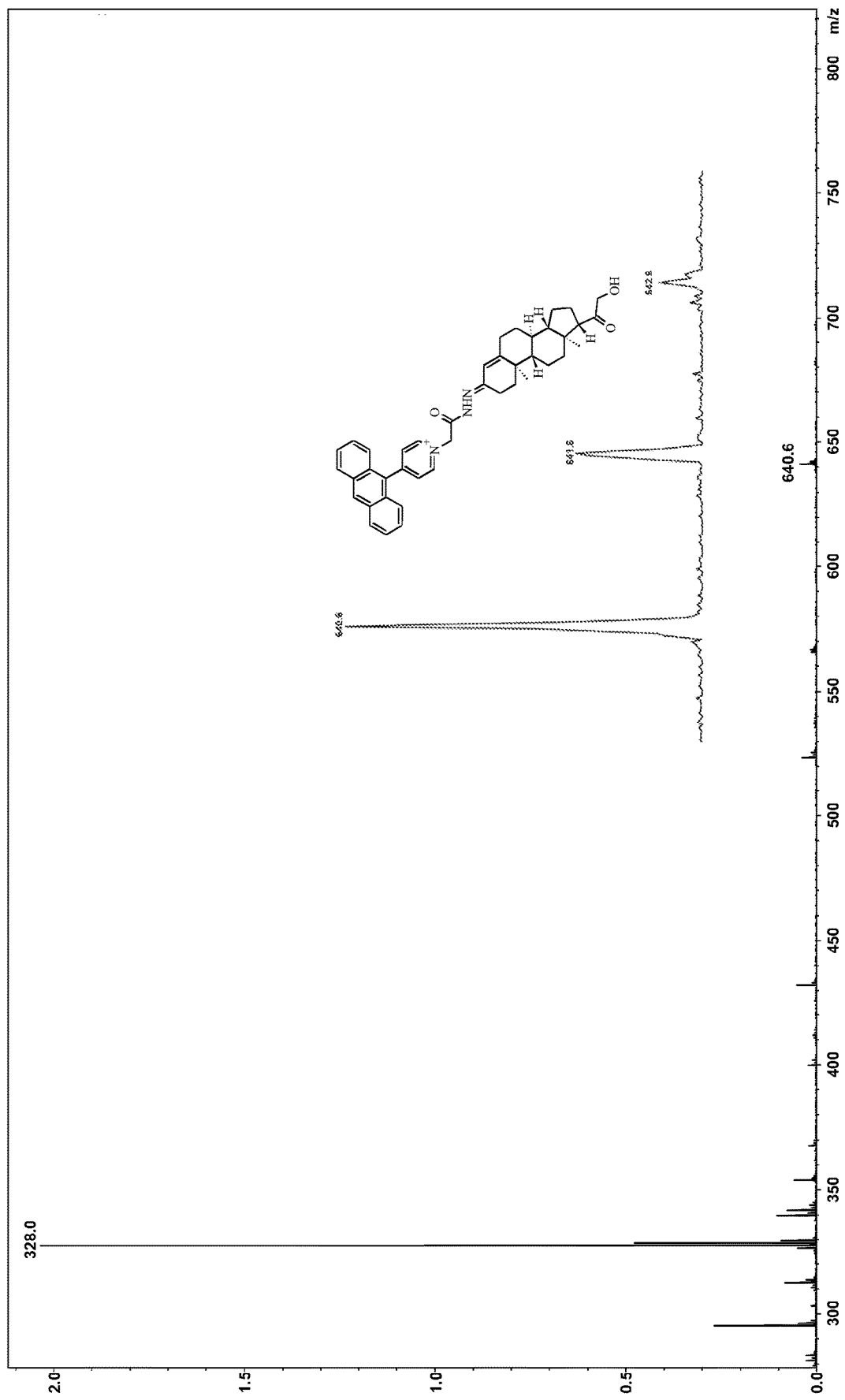
FIG. 4 is a MALDI mass spectrum illustrating detection of a hydrazone derivative of 11-deoxycorticostereone without addition of any additional assisting matrix

Example 4: Use of 4-(anthracen-9-yl)-1-(2-hydrazinyl-2-oxoethyl)pyridin-1-ium as a Reactive Matrix for the MALDI-MS Analysis of 11-deoxycorticosterone The synthesised 4-(anthracen-9-yl)-1-(2-hydrazinyl-2-oxoethyl)pyridin-1-ium reactive matrix was added to a sample of 11-deoxycorticosterone on a metal plate, and the resulting derivative was analysed directly by MALDI-MS operating in positive ion mode. The resulting MALDI spectrum is shown in FIG. 4. Peaks corresponding to the reactive matrix bound to 11-deoxycorticosterone as a hydrazone can clearly be observed at m/z=640.6. No additional assisting MALDI matrix substance was required in order to obtain the MALDI spectrum.

In control experiments without reactive matrix and using the traditional assisting matrix substance DHB, no signal for 11-deoxycorticosterone can be observed at the relevant sample concentrations.

Example 5: Synthesis and MALDI-MS Utility of Further Pyridinium Reactive Matrices The following compounds exemplify additional reactive matrices that may be prepared by the general methods A and/or C and those described below.

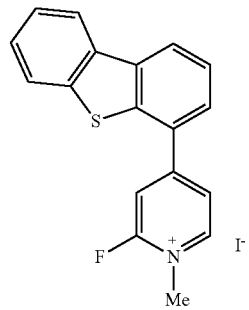

4-(Dibenzo[b,d]thiophen-4-yl)-2-fluoro-1-methylpyridin-1-ium iodide (14)

Prepared following the general procedures A and C, starting from 2-fluoro-4-bromopyridine.

$^1$H NMR (400 MHz, CD$_3$CN/CD$_3$Cl) δ 8.70 (dd, J=6.6, 5.0 Hz, 1H), 8.50 (dd, J=7.7, 1.3 Hz, 1H), 8.38-8.30 (m, 1H), 8.28 (dd, J=6.6, 2.0 Hz, 1H), 8.19 (dd, J=5.4, 2.0 Hz, 1H), 8.02-7.93 (m, 1H), 7.80 (dd, J=7.5, 1.4 Hz, 1H), 7.75 (dd, J=7.7, 7.6 Hz, 1H), 7.62-7.56 (m, 2H), 4.25 (d, J=3.6 Hz, 3H).

¹³C NMR (101 MHz, CD₃CN/CD₃Cl) δ 161.0 (d, J=11.2 Hz), 143.7 (d, J=7.1 Hz), 137.4, 137.1, 136.7, 134.0, 128.6 (d, J=2.0 Hz), 127.8, 127.3, 125.2, 124.7, 124.5, 122.1 (d, J=3.6 Hz), 122.0, 121.6, 111.8 (d, J=21.4 Hz), 40.8 (d, J=5.8 Hz).

MS (m/z) calc'd for $C_{18}H_{13}FNS^+$ ([M⁺]): 294.1 found, m/z 294.1.

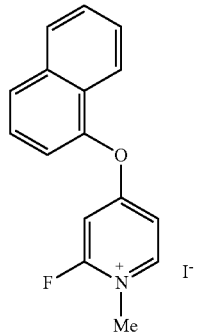

2-Fluoro-1-methyl-4-(naphthalen-1-yloxy)pyridin-1-ium iodide (15)

To a solution of 2,4-difluoropyridine (3.5 mmol) in DMF (4 mL) was added 1-naphthol (1.5 equiv) and K₂CO₃ (3 equiv). The resulting solution was stirred at room temperature for 18 hrs and subsequently extracted with EtOAc and brine. The intermediate 2-fluoro-4-(naphthalen-1-yloxy)pyridine was isolated by silica gel chromatography eluting with 5% EtOAc in n-Hexane. The title compound was prepared following the general procedure C, starting from 2-fluoro-4-(naphthalen-1-yloxy)pyridine. ¹H NMR (400 MHz, CD₃CN/CD₃Cl) δ 8.45 (ddd, J=7.2, 5.6, 1.3 Hz, 1H), 8.11 (d, J=8.9 Hz, 1H), 8.05-7.99 (m, 1H), 7.99-7.90 (m, 1H), 7.76 (d, J=2.5 Hz, 1H), 7.66-7.55 (m, 2H), 7.38-7.32 (m, 2H), 7.20 (dd, J=6.3, 2.6 Hz, 1H), 4.06 (d, J=3.5, 1.3 Hz, 3H).

¹³C NMR (101 MHz, CD₃CN/CD₃Cl) δ 175.1 (d, J=12.5 Hz), 161.7 (d, J=273.1 Hz), 150.8, 146.4 (d, J=5.4 Hz), 135.1, 133.3, 132.7, 129.1, 129.0, 128.6, 128.0, 120.3, 119.3, 113.6 (d, J=2.5 Hz), 101.5 (d, J=25.4 Hz), 41.7 (d, J=5.0 Hz).

MS (m/z) calc'd for $C_{16}H_{13}FNO^+$ ([M⁺]): 254.1 found, m/z 254.2.

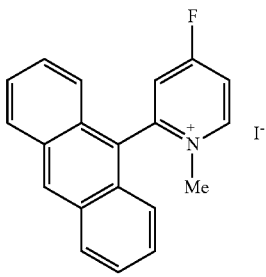

2-(Anthracen-9-yl)-4-fluoro-1-methylpyridin-1-ium iodide (16)

Prepared following the general procedures A and C, starting from 4-fluoro-2-bromopyridine.

¹H NMR (400 MHz, CD₃CN) δ 9.26 (dd, J=7.1, 5.5 Hz, 1H), 8.96 (s, 1H), 8.30-8.22 (m, 2H), 8.09 (td, J=6.9, 3.0 Hz, 1H), 7.95 (dd, J=7.0, 3.0 Hz, 1H), 7.68-7.55 (m, 4H), 7.44 (dq, J=8.0, 1.0 Hz, 2H), 3.78 (d, J=1.0 Hz, 3H).

¹³C NMR (101 MHz, CD₃CN) δ 173.3 (d, J=280.8 Hz), 159.0 (d, J=14.1 Hz), 153.3 (d, J=13.3 Hz), 132.9, 131.9, 130.3, 130.2, 129.7, 127.2, 124.7, 123.5, 121.5 (d, J=22.1 Hz), 117.2 (d, J=22.3 Hz), 46.8.

MS (m/z) calc'd for $C_{20}H_{15}FN^+$ ([M⁺]): 288.1 found, m/z 288.1.

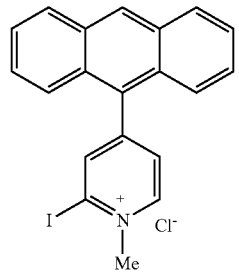

4-(Anthracen-9-yl)-2-iodo-1-methylpyridin-1-ium chloride (17)

Prepared following the general procedures A and C, starting from 4-fluoro-2-chloropyridine.

¹H NMR (400 MHz, DMSO-d₆) δ 9.46 (d, J=6.3 Hz, 1H), 8.91-8.82 (m, 2H), 8.29-8.18 (m, 3H), 7.65-7.59 (m, 2H), 7.59-7.52 (m, 4H), 4.54 (s, 3H).

MS (m/z) calc'd for $C_{20}H_{15}IN^+$ ([M⁺]): 396.0 found, m/z 396.0.

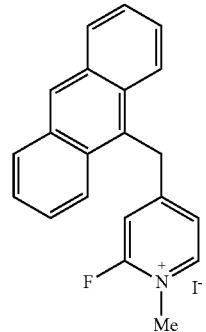

4-(Anthracen-9-ylmethyl)-2-fluoro-1-methylpyridin-1-ium iodide (18)

Prepared following the general procedures A and C, starting from 2-fluoropyridin-4-ylboronic acid and 9-(bromomethyl)anthracene. ¹H NMR (400 MHz, CD₃CN) 8.67 (s, 1H), 8.33 (dd, J=6.6, 4.8 Hz, 1H), 8.21-8.11 (m, 4H), 7.64-7.51 (m, 5H), 7.47-7.42 (m, 1H), 5.35 (s, 2H), 4.04 (d, J=3.6 Hz, 3H).

¹³C NMR (101 MHz, CD₃CN) δ 169.2 (d, J=11.2 Hz), 158.5 (d, J=280.5 Hz), 144.4 (d, J=6.6 Hz), 132.7, 131.3, 130.4, 129.3, 128.1, 128.0, 126.4, 124.8, 124.7 (d, J=3.2 Hz), 114.2 (d, J=20.5 Hz), 42.1 (d, J=5.4 Hz), 34.4 (d, J=1.8 Hz).

MS (m/z) calc'd for $C_{21}H_{17}FN^+$ ([M⁺]): 302.1 found, m/z 302.2.

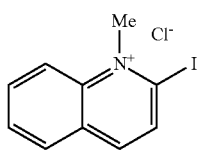 [SMILES: C[n+]1c(I)ccc2ccccc21 ; [Cl-]]

2-Iodo-1-methylquinolinium chloride (19)

Prepared following the general procedures C, starting from 2-chloroquinoline. $^1$H NMR (400 MHz DMSO-$d_6$) δ 7.90 (d, J=9.4 Hz, 1H), 7.72 (dd, J=7.7, 1.6 Hz, 1H), 7.63 (ddd, J=8.7, 7.1, 1.6 Hz, 1H), 7.53 (d, J=8.5 Hz, 1H), 7.27 (ddd, J=7.7, 7.1, 1.1 Hz, 1H), 6.61 (d, J=9.5 Hz, 1H), 3.61 (s, 3H);
$^{13}$C NMR (101 MHz, DMSO-$d_6$) 161.1, 139.7, 139.2, 130.8, 128.7, 121.9, 121.1, 120.1, 114.6, 29.0.
MS (m/z) calc'd for $C_{10}H_9N^+$ ([M$^+$]): 270.0 found, m/z 270.0.

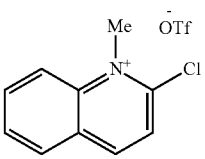 [SMILES: C[n+]1c(Cl)ccc2ccccc21]

2-Chloro-1-methylquinolin-1-ium trifluoromethanesulfonate (20)

Prepared following the general procedure C, starting from 2-chloroquinoline and methyl trifluoromethanesulfonate. $^1$H NMR (400 MHz, DMSO-$d_6$) δ 7.89 (d, J=9.5 Hz, 1H), 7.71 (dd, J=7.7, 1.6 Hz, 1H), 7.62 (ddd, J=8.6, 7.1, 1.6 Hz, 1H), 7.52 (dd, J=8.5, 0.9 Hz, 1H), 7.26 (ddd, J=7.9, 7.2, 1.1 Hz, 1H), 6.60 (d, J=9.4 Hz, 1H), 3.61 (s, 3H).
$^{13}$C NMR (101 MHz, DMSO-$d_6$) 161.2, 139.8, 139.3, 130.9, 128.8, 122.0, 121.1, 120.2, 114.7, 29.1.
MS (m/z) calc'd for $C_{10}H_9ClN^+$ ([M$^+$]): 178.0 found, m/z 178.0.

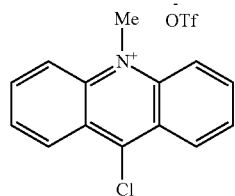 [SMILES: C[n+]1c2ccccc2c(Cl)c2ccccc21]

9-Chloro-10-methylacridin-10-ium trifluoromethanesulfonate (21)

Prepared following the general procedure C, starting from 9-chloroacridine and methyl trifluoromethanesulfonate. $^1$H NMR (400 MHz, (CD$_3$)$_2$CO) δ 9.01 (ddd, J=8.7, 1.5, 0.6 Hz, 2H), 8.97 (dt, J=9.3, 0.8 Hz, 2H), 8.60 (ddd, J=9.3, 6.8, 1.5 Hz, 2H), 8.23 (ddd, J=8.7, 6.8, 0.9 Hz, 2H), 5.12 (s, 3H); $^{13}$C NMR (101 MHz, DMSO-$d_6$/(CD$_3$)$_2$CO) 177.3, 143.2, 134.4, 127.3, 122.6, 121.6, 116.5, 34.0.

MS (m/z) calc'd for $C_{14}H_{11}ClN^+$ ([M$^+$]): 228.1 found, m/z 228.1.

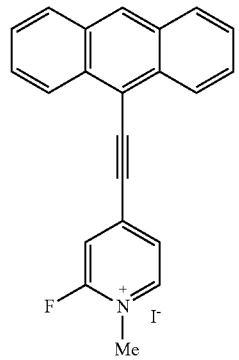

4-(Anthracen-9-ylethynyl)-2-fluoro-1-methylpyridin-1-ium iodide (22)

9-(Prop-1-yn-1-yl)anthracene (1 equiv), CuI (0.11 equiv), Pd(PPh$_3$)$_2$Cl$_2$ (0.1 equiv), 4-Bromo-2-fluoropyridine (2.7 equiv) were dissolved in dry TEA (15 mL) and the reaction mixture was stirred at 110° C. overnight. After cooling to room temperature, 100 mL of sat. NH$_4$Cl solution was added and the aqueous phase was extracted three times with 100 mL diethyl ether. The combined organic phases were dried over Na$_2$SO$_4$ and concentrated under vacuum. The crude mixture was purified by column chromatography (silica gel, pentane+5% toluene and 2-5% EtOAc) to give the intermediate 4-(anthracen-9-ylethynyl)-2-fluoropyridine. The title compound was prepared following the general procedure C, starting from 4-(anthracen-9-ylethynyl)-2-fluoropyridine. $^1$H NMR (400 MHz, DMSO-$d_6$) δ 9.01 (dd, J=6.6, 5.1 Hz, 1H), 8.97 (s, 1H), 8.76 (dd, J=5.6, 1.8 Hz, 1H), 8.72 (dd, J=8.7, 1.0 Hz, 2H), 8.48 (dd, J=6.5, 1.8 Hz, 1H), 8.27 (dd, J=8.4, 1.1 Hz, 2H), 7.82 (ddd, J=8.7, 6.6, 1.3 Hz, 2H), 7.71 (ddd, J=8.0, 6.6, 1.2 Hz, 2H), 4.21 (d, J=3.7 Hz, 3H).
MS (m/z) calc'd for $C_{22}H_{15}FN^+$ ([M$^+$]): 312.1 found, m/z 312.1.

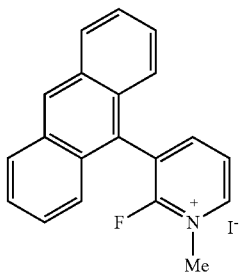

3-(Anthracen-9-yl)-2-fluoro-1-methylpyridin-1-ium iodide (23)

Prepared following the general procedures A and C, starting from 2-fluoro-3-bromopyridine.
$^1$H NMR (400 MHz, DMSO-$d_6$) δ 9.25-9.17 (m, 1H), 8.94 (s, 1H), 8.93-8.85 (m, 1H), 8.30-8.22 (m, 3H), 7.71 (d, J=8.7 Hz, 2H), 7.64 (ddd, J=8.3, 6.6, 1.6 Hz, 2H), 7.58 (ddd, J=8.3, 6.6, 1.6 Hz, 2H).

MS (m/z) calc'd for $C_{20}H_{15}FN^+$ ([M$^+$]): 288.1 found, m/z 288.2.

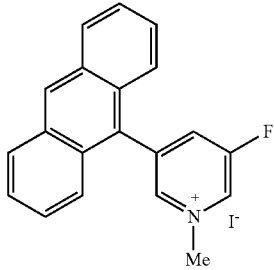

3-(Anthracen-9-yl)-5-fluoro-1-methylpyridin-1-ium iodide (24)

Prepared following the general procedures A and C, starting from 5-fluoro-3-bromopyridine.

$^1$H NMR (400 MHz, DMSO-d$_6$) δ 9.66 (ddd, J=3.9, 2.4, 1.1 Hz, 1H), 9.22 (dd, J=1.30, 1.26 Hz, 1H), 8.95 (ddd, J=8.2, 2.5, 1.4 Hz, 1H), 8.91 (s, 1H), 8.26 (ddd, J=8.4, 1.4, 0.7 Hz, 2H), 7.70-7.60 (m, 4H), 7.56 (ddd, J=8.7, 6.6, 1.4 Hz, 2H), 4.45 (s, 3H).

$^{13}$C NMR (101 MHz, CDCl$_3$/CD$_3$CN) δ 161.1 (d, J=257.2 Hz), 144.6, 141.6 (d, J=7.6 Hz), 136.2 (d, J=17.6 Hz), 135.7 (d, J=36.8 Hz), 131.7, 130.7, 130.6, 129.5, 128.1, 126.6, 126.5, 125.7, 50.0.

MS (m/z) calc'd for $C_{20}H_{15}FN^+$ ([M$^+$]): 288.1 found, m/z 288.2.

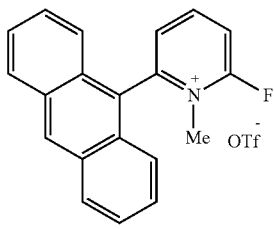

2-(Anthracen-9-yl)-6-fluoro-1-methylpyridin-1-ium trifluoromethanesulfonate (25)

Prepared following the general procedures A and C, starting from 2-fluoro-6-bromopyridine.

$^1$H NMR (400 MHz, CD$_3$CN) 8.95 (s, 1H), 8.82 (dd, J=7.5, 7.0 Hz, 1H), 8.27 (d, J=7.7 Hz, 2H), 8.07 (dd, J=8.9, 4.5 Hz, 1H), 8.02-7.94 (m, 1H), 7.70-7.56 (m, 4H), 7.47 (d, J=8.1 Hz, 2H), 3.67 (d, J=3.9 Hz, 3H).

$^{13}$C NMR (101 MHz, CD$_3$CN) δ 161.8 (d, J=281.4 Hz), 153.8 (d, J=8.4 Hz), 151.5 (d, J=12.8 Hz), 133.0, 132.0, 131.0, 130.3, 129.6, 129.4, 129.3, 127.3, 124.8, 115.5 (d, J=21.6 Hz), 39.0 (d, J=6.6 Hz).

MS (m/z) calc'd for $C_{20}H_{15}FN^+$ ([M$^+$]): 288.1 found, m/z 288.2.

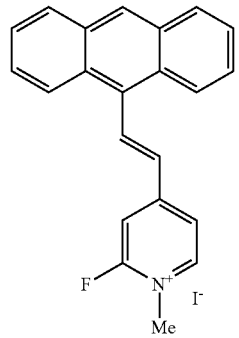 [SMILES: C[n+]1ccc(/C=C/c2c3ccccc3cc3ccccc23)cc1F ; [I-]]

(E)-4-(2-(Anthracen-9-yl)vinyl)-2-fluoro-1-methylpyridin-1-ium iodide (26)

To an oven-dried, glass vessel was added Pd$_2$(dba)$_3$ (0.01 eq), Cy$_3$P (0.04 eq) and 4-(anthracen-9-ylethynyl)-2-fluoro-pyridine (1 eq). The vessel was sealed and flushed with N$_2$ three times before 0.2 mL of 1,4-dioxane was added. After stirring the mixture at room temperature for 15 min, 25% aqueous formic acid (3 equiv) was added and the reaction was heated to 80° C. After 2 hours, the solvent was removed under vacuo and the residue was purified by column chromatography (pentane, 5% toluene and 2-5% EtOAc) to afford the intermediate (E)-4-(2-(anthracen-9-yl)vinyl)-2-fluoro-pyridine. The title compound was prepared following the general procedures A and C, starting from (E)-4-(2-(anthracen-9-yl)vinyl)-2-fluoro-pyridine. $^1$H NMR (400 MHz, DMSO-d$_6$) δ 9.03 (d, J=16.4 Hz, 1H), 8.91 (dd, J=6.6, 5.1 Hz, 1H), 8.74 (s, 1H), 8.56 (dd, J=6.2, 1.8 Hz, 1H), 8.41-8.35 (m, 3H), 8.23-8.15 (m, 2H), 7.67-7.56 (m, 4H), 7.36 (d, J=16.5 Hz, 1H), 4.19 (d, J=3.6 Hz, 3H).

MS (m/z) calc'd for $C_{22}H_{17}FN^+$ ([M$^+$]): 314.1 found, m/z 314.2.

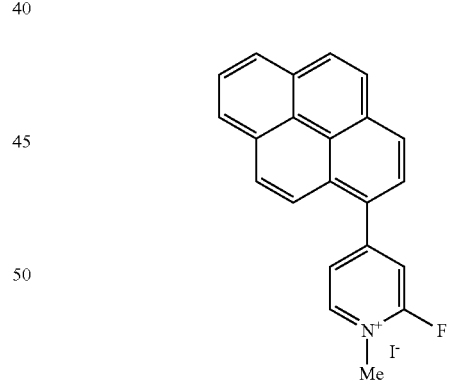

2-Fluoro-1-methyl-4-(pyren-1-yl)pyridin-1-ium iodide (27)

Prepared following the general procedures A and C, starting from 4-fluoro-2-bromopyridine.

$^1$H NMR (400 MHz, DMSO-d$_6$) δ 9.09 (dd, J=6.5, 5.0 Hz, 1H), 8.58 (dd, J=5.5, 1.9 Hz, 1H), 8.52 (d, J=8.1 Hz, 1H), 8.48-8.42 (m, 2H), 8.41-8.30 (m, 4H), 8.23-8.17 (m, 3H), 4.32 (d, J=3.7 Hz, 3H).

MS (m/z) calc'd for $C_{22}H_{15}FN^+$ ([M$^+$]): 312.1 found, m/z 312.2.

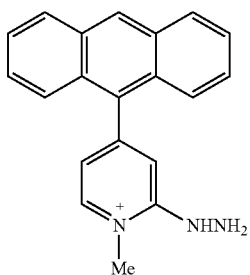

4-(Anthracen-9-yl)-2-hydrazineyl-1-methylpyridin-1-ium (28)

To a solution of 4-(anthracen-9-yl)-2-fluoro-1-methylpyridinium iodide (10 mg, 0.036 mmol) in acetonitrile was added tert-butyl carbazate (5 mg, 0.036 mmol). The resulting mixture was stirred for 1 hour and then washed with water and ethylacetate. The combined organic layers were then evaporated with reduced vacuum to yield the crude protected intermediate. This residue was taken up in 0.2 mL of 4M HCl in dioxane and stirred at room temperature for 48 hours. The mixture was then extracted with Ethylacetate and water. The combined water layers were evaporated with reduced vacuum to yield a yellow solid (3 mg, 40%). $^1$H NMR (400 MHz, DMSO-de) 8.69 (s, 1H), 8.23-8.06 (m, 2H), 7.91 (d, J=6.8 Hz, 1H), 7.74 (dq, J=8.4, 1.0 Hz, 2H), 7.63-7.39 (m, 4H), 6.41 (dd, J=1.9, 0.6 Hz, 1H), 6.26 (dd, J=6.8, 1.9 Hz, 1H), 3.59 (s, 3H), 3.56 (s, 4H).

$^{13}$C NMR (101 MHz, DMSO-de) 162.1, 150.7, 140.4, 133.6, 131.2, 129.1, 128.6, 127.7, 126.8, 125.9, 121.1, 108.9, 37.28.

MS (m/z) calc'd for $C_{20}H_{18}N_3^+$ ([M]$^+$) m/z 300.2, found m/z 300.2

To evaluate the efficiency of the synthesized substances as reactive matrices for high sensitivity MALDI-MSI analysis, small molecules with primary amine, and/or phenolic groups were used as test substances. Two concentrations (0.1 mg/ml and 0.01 mg/ml) of serotonin (5-HT), dopamine (DA), 3,4-dihydroxyphenylacetic acid (DOPAC), 3-O-Methyldopa (3-OMD) and γ-aminobutyric acid (GABA) were deposited (0.5 µl) on a MALDI metal target. The reactive matrix solutions were prepared by dissolving the synthesized compounds in 70% acetonitrile (4.4 mM). An automated pneumatic sprayer (TM-Sprayer, HTX technologies) was used to spray 5 ml of heated reagent over the spotted standards. The nozzle temperature was set at 80° C. and the reagent was sprayed in 30 passes at a flow of 80 µl/min. MSI data was acquired in positive ionization mode on a MALDI-FT-ICR (Solarix XR 7T-2Ω, Bruker Daltonics) instrument by rastering across the spots at a spatial resolution of 250 µm. Signal to noise (S/N) values for all derivatized compounds were extracted from the average spectrum of each spot using an in-house developed software (msIQuant). The results are shown in Table 2 below.

TABLE 2

| Test reactive matrix name | Analyte of Interest | | | | |
|---|---|---|---|---|---|
| | 5HT | 3-OMD | DA | DOPAC | GABA |
| 4-(Dibenzo[b,d]thiophen-4-yl)-2-fluoro-1-methylpyridin-1-ium iodide (14) | Y | Y | Y | Y | Y |
| 2-Fluoro-1-methyl-4-(naphthalen-1-yloxy)pyridin-1-ium iodide (15) | Y | Y | Y | Y | Y |
| 2-(Anthracen-9-yl)-4-fluoro-1-methylpyridin-1-ium iodide (16) | Y | Y | Y | Y | Y |
| 4-(Anthracen-9-yl)-2-iodo-1-methylpyridin-1-ium iodide (17) | N | Y | Y | Y | Y |
| 4-(Anthracen-9-ylmethyl)-2-fluoro-1-methylpyridin-1-ium iodide (18) | Y | Y | Y | Y | Y |
| 2-Iodo-1-methylquinolin-1-ium chloride (19) | Y | Y | Y | Y | Y |
| 2-Chloro-1-methylquinolin-1-ium trifluoromethanesulfonate (20) | Y | Y | Y | Y | N |
| 9-Chloro-10-methylacridin-10-ium trifluoromethanesulfonate (21) | Y | Y | Y | Y | N |
| 4-(Anthracen-9-ylethynyl)-2-fluoro-1-methylpyridin-1-ium iodide (22) | Y | Y | Y | Y | Y |
| 3-(Anthracen-9-yl)-2-fluoro-1-methylpyridin-1-ium iodide (23) | Y | Y | Y | Y | Y |
| 3-(Anthracen-9-yl)-5-fluoro-1-methylpyridin-1-ium iodide (24) | Y | Y | Y | Y | Y |
| 2-(Anthracen-9-yl)-6-fluoro-1-methylpyridin-1-ium trifluoromethanesulfonate (25) | Y | Y | Y | Y | Y |
| (E)-4-(2-(Anthracen-9-yl)vinyl)-2-fluoro-1-methylpyridin-1-ium iodide (26) | Y | Y | Y | Y | Y |
| 2-Fluoro-1-methyl-4-(pyren-1-yl)pyridin-1-ium iodide (27) | Y | Y | Y | Y | Y |

Y = S/N greater than 3; N = S/N less than 3.

As can be seen from Table 2 all synthesized reactive matrices were effective in promoting the ionization and desorption of a range of analytes.

Example 6: Use of Bromo-Pyrylium Reactive Matrices for the MALDI-MSI Detection of Drugs in Brain Tissue Sections Charge-tagging through pyrylium derivatization has been proven to increase the sensitivity for MALDI and DESI-MSI analysis of primary amine containing small molecules. Since such derivatization adds just carbon and hydrogen to the target compounds, the resulted isotopic patterns of the products are not distinctive from those species which are not derivatized but ionized, desorbed and detected unselectively. By addition of bromine to the substituted pyrylium ion, this results in a distinctive isotopic pattern and mass defect for derivatized substances which makes them distinguishable from underivatized compounds.

Material and Reagents

Tetrafluoroborate salts of 2,4,6-triphenylpyrylium (TPP) and 2-(4-bromo-phenyl)-4,6-diphenyl-pyranylium (Br- TPP), triethylamine (TEA), and all other chemicals were purchased from Sigma-Aldrich (Stockholm, Sweden) unless otherwise stated and were used without further purification. Water, methanol, and trifluoroacetic acid (TFA) were obtained from Merck (Hohenbrunn, Germany).

Animal Experiments

All animals were housed in air-conditioned rooms (with a 12 h dark/light cycle) at 20° C. and 53% humidity, with access to food and water ad libitum. Experiments were performed in accordance with the European Communities Council Directive of Nov. 24, 1986 (86/609/EEC) on the ethical use of animals and were approved by the local ethical committee at the Karolinska Institute (N350/08 and N40/13).

Adult male C57BL/6 mice (3 months old, Charles River Laboratories, Köln, Germany) were used for experiments with fluvoxamine. Fluvoxamine was dissolved in 0.25% tween 80/saline and injected i.p. at a dose of 40 mg/kg. Mice were sacrificed by cervical dislocation 30 min after fluvoxamine administration. Vehicle control was obtained by injecting mouse with a volume of saline equal to that administered in the experimental treatment. All brains were immediately removed, snap frozen, and stored at −80° C. until further analysis.

Tissue Preparation and Derivatization

The frozen brain tissues were cut using a cryostat-microtome (Leica CM3050S; Leica Microsystems, Welzlar, Germany) at a thickness of 14 μm, thaw-mounted onto conductive indium tin oxide (ITO) glass slides (Bruker Daltonics), and stored at −80° C. Sections were dried gently under a flow of nitrogen and desiccated at room temperature for 15 min, after which they were imaged optically using a photo scanner (Epson perfection V500).

Brain samples were then coated with TPP and Br-TPP. Derivatization solutions were prepared by dissolving 8 mg of TPP or Br-TPP in 6 ml of 80% MeOH containing 3.5 μL of TEA. An automated pneumatic sprayer (TM-Sprayer; HTX Technologies, Carrboro, N.C.) was used to spray warm reagent over the tissue sections. The nozzle temperature was set at 80° C., and the reagent was sprayed in 30 passes over the tissue sections at a linear velocity of 110 cm/min with a flow rate of 80 μL/min. Samples were incubated for 15 min (dried by nitrogen flow every 5 m) in a chamber saturated with vapour from a 50% methanol solution before analysis.

Mass Spectrometry

All MALDI-MSI experiments were performed using a MALDI-TOF/TOF (Ultraflextreme, Bruker Daltonics, Bremen, Germany) mass spectrometer with a Smartbeam II 2 kHz laser in positive ion mode. The laser power was optimized at the start of each run and then held constant during the MALDI-MSI experiment. Fleximaging v 4.0 build 32 (Bruker Daltonics, Billerica, Mass.) was used for normalization and visualization of MALDI-MSI data.

Results

Figure 5:
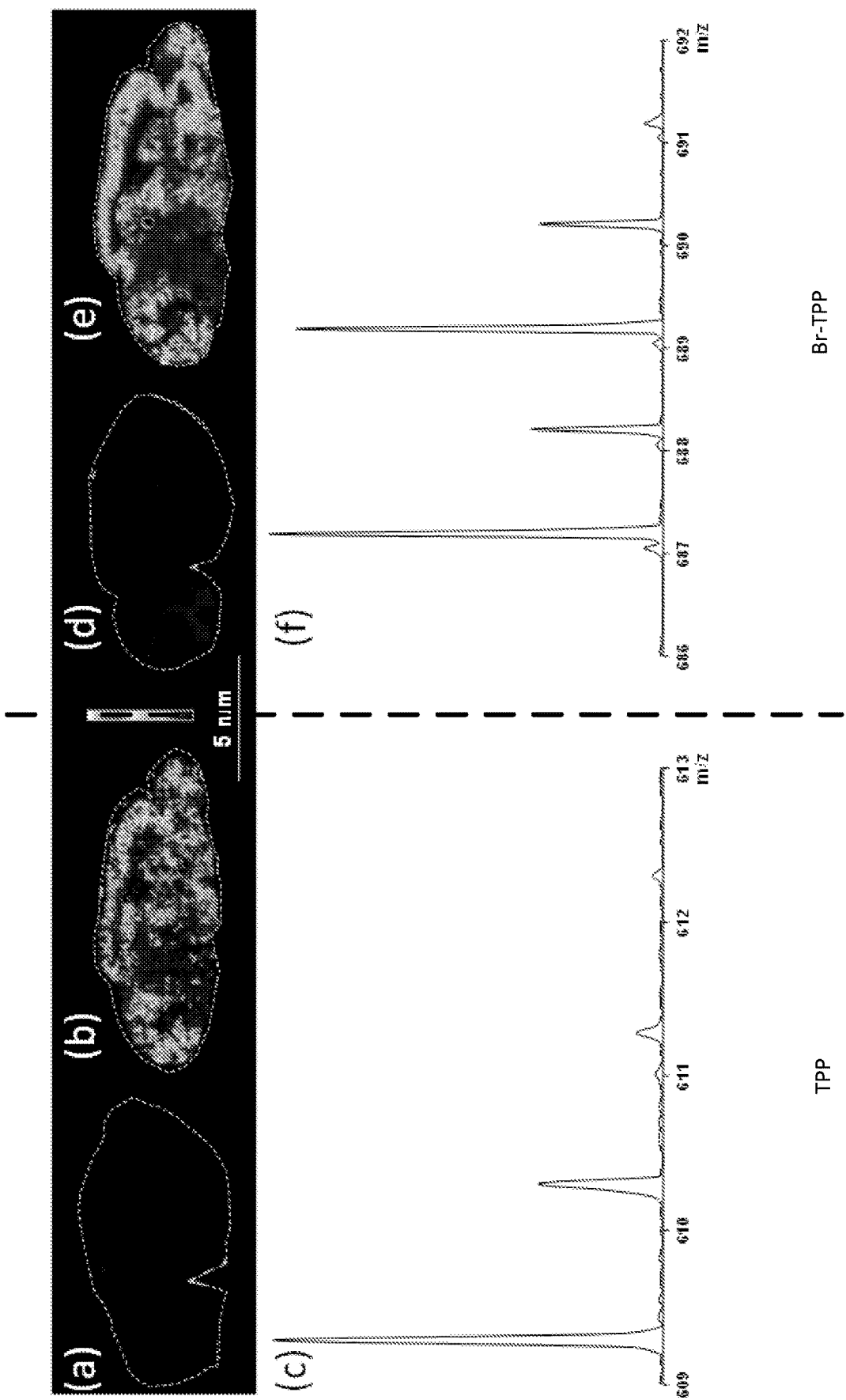
FIG. 5 is a series of images (a)-(f) illustrating the MALDI-MSI analysis of fluvoxamine in mouse brain tissue sections

TPP and its brominated derivative, Br-TPP, were used to map the localization of fluvoxamine in mouse brain tissue sections, see FIG. 5. FIG. 5 shows the MALDI-MSI relative abundance and spatial distribution of TPP (a, b) and Br-TPP (d, e) derivatized fluvoxamine (m/z 609.3 and 687.2) in control (a, d) and administered (b, e) brain tissue sections without any assisting matrix. FIG. 5 also shows the average spectra of TPP (c) and Br-TPP (f) treated fluvoxamine-administered tissue section. Data are shown using a rainbow scale, normalized against the total ion count. Scale bar, 5 mm; spatial resolution=100 μm.

Fluvoxamine is a selective serotonin reuptake inhibitor (SSRI) that was originally developed as an antidepressant but is commonly used for treatment of anxiety disorders. The primary amine functional group of fluvoxamine reacts selectively with both TPP and Br-TPP. Brain tissue sections from control and fluvoxamine administered mice were derivatized by non-brominated TPP (a, b) and brominated Br-TPP (d, e). No interfering signal was detected in control brain tissue section using TPP (a) and Br-TPP (d) while derivatized fluvoxamine was detected at m/z 609.3 using TPP (b) and at m/z 687.2 using Br-TPP (e) without any assisting matrix. Similar distribution of fluvoxamine, mostly localized in cortex and cerebellum, was found using both derivatization agents. The isotopic pattern of TPP derivatized fluvoxamine represents a typical non-labelled compound (c) while bromine containing Br-TPP derivatized fluvoxamine demonstrates a specific isotopic pattern that can be easily distinguished from signals corresponding to non-derivatized substances.

The invention claimed is:

1. A compound of formula II or a salt thereof:

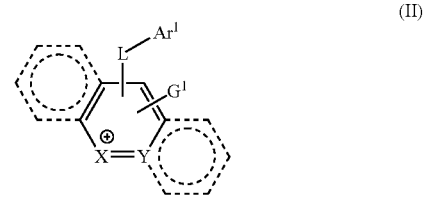

(II)

wherein:

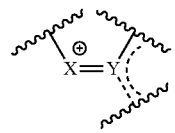

is selected from the group consisting of

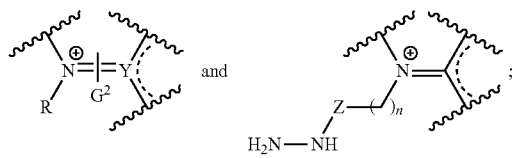

- —$Ar^1$ is optionally substituted and is selected from the group consisting of biphenyl, terphenyl, $C_{10}$-$C_{30}$ polycyclic aromatic hydrocarbon and $C_6$-$C_{30}$ heteroaryl analogue of a polycyclic aromatic hydrocarbon;
- -L- is selected from a bond, —$(CH_2)_m$— or any π-conjugating linker moiety selected from the group consisting of —O—, —S—, —NH—,

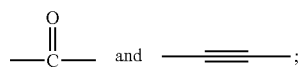

- -$G^1$ is selected from —H, -Me or —$Ar^2$;
- —R is a $C_1$-$C_{15}$ alkyl group optionally labelled with one or more D, T, or $^{13}$C atoms;

-G² is selected from the group consisting of —F, —Cl, —Br, —I and —(CH₂)ₙ—Z—NH—NH₂;

m and n are each independently from 0 to 15;

—Z— is selected from a bond, —CH₂— or —C(O)—; and

Ar² is optionally substituted and is selected from the group consisting of phenyl, biphenyl, terphenyl, C₁₀-C₃₀ polycyclic aromatic hydrocarbon, and C₄-C₃₀ mono- or polycyclic heteroaryl.

2. Compound according to claim 1, wherein the compound of formula II has a formula IIa or IIb,

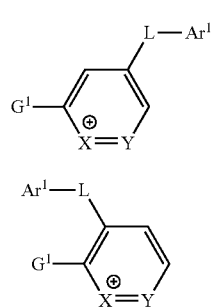

and wherein

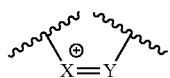

is selected from the group consisting of

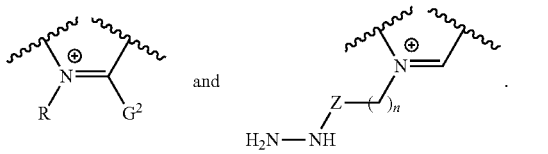

3. Compound according to claim 1, wherein each of Ar¹ and Ar² is optionally independently substituted with one or more substituents selected from the group consisting of -D, -T, —F, —Cl, —Br, —I, —NO₂, —CN, —R'", —OR'", —OC(O)R'", —SR'", —S(O)R'", —S(O)(O)R'" and —NR'"R"", wherein —R'" and —R"" are each independently selected from phenyl, tolyl and C₁-C₁₅ alkyl.

4. Compound according to claim 1, wherein Ar¹ is optionally substituted with one or more -Ph, —Cl or —Br groups and is selected from the group consisting of biphenyl, terphenyl, naphthalene, anthracene, phenanthrene, and pyrene.

5. Compound according to claim 1, wherein-G¹ is —H.

6. Compound according to claim 1, wherein the compound of formula II, IIa or IIb is

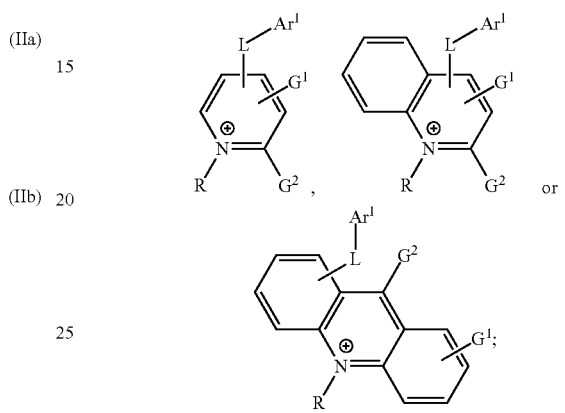

wherein

—R is optionally labelled with one or more deuterium, tritium, or carbon-13 atoms and is selected from the group consisting of methyl, ethyl, n-propyl and n-butyl; and -G² is selected from the group consisting of —F, —Cl, —Br and —I.

7. Compound according to claim 1, wherein

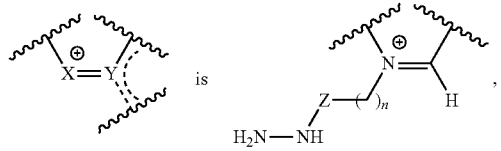

Z is C=O, and wherein n is from 1 to 3.

* * * * *